United States Patent
Sutherland et al.

(10) Patent No.: US 7,619,739 B1
(45) Date of Patent: Nov. 17, 2009

(54) DETECTION AND IDENTIFICATION OF BIOLOGICAL AGENTS USING BRAGG FILTERS

(75) Inventors: Richard L. Sutherland, Bellbrook, OH (US); Donna M. Brandelik, New Carlisle, OH (US); Christina K. Shepherd, Beavercreek, OH (US)

(73) Assignee: Science Applications International Corporation, San Diego, CA (US)

( * ) Notice: Subject to any disclaimer, the term of this patent is extended or adjusted under 35 U.S.C. 154(b) by 402 days.

(21) Appl. No.: 10/614,188

(22) Filed: Jul. 8, 2003

Related U.S. Application Data

(60) Provisional application No. 60/406,665, filed on Aug. 29, 2002.

(51) Int. Cl.
*G01N 21/59* (2006.01)

(52) U.S. Cl. .................. 356/432; 356/445; 436/535; 422/82.05

(58) Field of Classification Search ............. 356/39–42, 356/432, 445–448; 436/535; 422/82.05; 122/82.05
See application file for complete search history.

(56) References Cited

U.S. PATENT DOCUMENTS

| | | | |
|---|---|---|---|
| 3,580,655 A | 5/1971 | Leith et al. .................. 350/3.5 |
| 3,658,526 A | 4/1972 | Haugh .......................... 96/27 |
| 3,667,946 A | 6/1972 | Sturdevant .................. 96/35.1 |
| 3,758,186 A | 9/1973 | Brumm ....................... 350/3.5 |
| 4,003,629 A | 1/1977 | Baues et al. ............... 350/96 C |
| 4,006,963 A | 2/1977 | Baues et al. ............... 350/96 C |
| 4,018,228 A | 4/1977 | Goosen ....................... 128/305 |
| 4,045,124 A | 8/1977 | Pollack et al. .......... 350/160 LC |
| 4,124,947 A | 11/1978 | Kuhl et al. .................... 40/453 |
| 4,210,132 A | 7/1980 | Perlin .......................... 128/1 R |
| 4,368,736 A | 1/1983 | Kaster .................... 128/334 C |

(Continued)

FOREIGN PATENT DOCUMENTS

CA 544591 8/1957

(Continued)

OTHER PUBLICATIONS

Evanescent Wave Long-Period Fiber Bragg Grating as an Immobilized Antibody Biosensor DeLisa, M.P., Zhang, Z., Shiloach, M., Pilevar, S., Davis, C.C., Sirkis, J.S., and Bentley, W.E. Anal. Chem., 72, 13, 2895 - 2900, 2000, 10.1021/ac9912395.*

(Continued)

*Primary Examiner*—Gregory J Toatley, Jr.
*Assistant Examiner*—Rebecca C Slomski
(74) *Attorney, Agent, or Firm*—King & Spalding LLP

(57) ABSTRACT

A method of sensing an environmental agent, comprising obtaining a sample from the environment and transferring the sample into the working fluid for dispensation to a detection module. The sample and working fluid mixture is filtered through a porous polymer Bragg grating. By comparing the refractive index of the grating with the mixture to the refractive index of a grating without the sample, a difference in the refractive index aids in the identification of a hazardous agent in the environment. The sensor also acts as a chemical filter by trapping specific target agents by a highly specific reaction with a conjugate molecule. Recirculation of the working fluid throughout the system provides a sensor that is "always on."

35 Claims, 25 Drawing Sheets

U.S. PATENT DOCUMENTS

| | | | |
|---|---|---|---|
| 4,374,371 A | 2/1983 | Narancic | 337/159 |
| 4,416,540 A | 11/1983 | Nicholson | 350/3.69 |
| 4,560,249 A | 12/1985 | Nishiwaki et al. | 350/162.17 |
| 4,673,241 A | 6/1987 | Nishiwaki et al. | 359/4 |
| 4,688,900 A | 8/1987 | Doane et al. | 350/347 V |
| 4,728,547 A | 3/1988 | Vaz et al. | 428/1 |
| 4,809,713 A | 3/1989 | Grayzel | 128/785 |
| 4,810,063 A | 3/1989 | Fergason | 350/347 V |
| 4,818,070 A | 4/1989 | Gunjima et al. | 350/334 |
| 4,832,424 A | 5/1989 | McGrew | 350/3.65 |
| 4,844,613 A * | 7/1989 | Batchelder et al. | 356/445 |
| 4,856,876 A | 8/1989 | Fergason | 350/350 F |
| 4,857,425 A | 8/1989 | Phillips | 430/1 |
| 4,891,152 A | 1/1990 | Miller et al. | 252/299.01 |
| 4,923,269 A | 5/1990 | Healey | 350/96.15 |
| 4,929,240 A | 5/1990 | Kirsch et al. | 606/151 |
| 4,930,674 A | 6/1990 | Barak | 227/179 |
| 4,938,568 A | 7/1990 | Margerum et al. | 350/334 |
| 4,942,102 A | 7/1990 | Keys et al. | 430/1 |
| 4,983,176 A | 1/1991 | Cushman et al. | 606/151 |
| 5,003,386 A | 3/1991 | Doyle et al. | 358/90 |
| 5,011,624 A | 4/1991 | Yamagishi et al. | 252/299.5 |
| 5,014,709 A | 5/1991 | Bjelkhagen et al. | 128/654 |
| 5,015,249 A | 5/1991 | Nakao et al. | 606/142 |
| 5,047,040 A | 9/1991 | Simpson et al. | 606/159 |
| 5,084,203 A | 1/1992 | Sansone et al. | 252/299.5 |
| 5,096,282 A | 3/1992 | Margerum et al. | 359/3 |
| 5,105,298 A | 4/1992 | Schellenberg | 359/3 |
| 5,136,666 A | 8/1992 | Anderson et al. | 385/24 |
| 5,144,690 A | 9/1992 | Domash | 385/12 |
| 5,166,813 A | 11/1992 | Metz | 359/15 |
| 5,170,925 A | 12/1992 | Madden et al. | 227/175 |
| 5,174,276 A | 12/1992 | Crockard | 128/4 |
| 5,182,180 A | 1/1993 | Gambogi, Jr. et al. | 430/1 |
| 5,182,665 A | 1/1993 | O'Callaghan et al. | 359/95 |
| 5,188,638 A | 2/1993 | Tzakis | 606/153 |
| 5,198,912 A | 3/1993 | Ingwall et al. | 359/3 |
| 5,210,630 A | 5/1993 | Heynderickx et al. | 359/106 |
| 5,227,859 A | 7/1993 | Leib et al. | 556/347 |
| 5,227,906 A | 7/1993 | Tokumitsu | 359/117 |
| 5,234,447 A | 8/1993 | Kaster et al. | 606/153 |
| 5,235,445 A | 8/1993 | Hirai et al. | 359/52 |
| 5,240,636 A | 8/1993 | Doane et al. | 252/299.01 |
| 5,258,008 A | 11/1993 | Wilk | 606/219 |
| 5,264,950 A | 11/1993 | West et al. | 359/51 |
| 5,270,843 A | 12/1993 | Wang | 359/52 |
| 5,272,550 A | 12/1993 | Dickson et al. | 359/3 |
| 5,291,317 A | 3/1994 | Newswanger | 359/15 |
| 5,299,289 A | 3/1994 | Omae et al. | 359/95 |
| 5,303,322 A | 4/1994 | Winston et al. | 385/146 |
| 5,313,317 A | 5/1994 | Saburi et al. | 359/13 |
| 5,323,251 A | 6/1994 | Coates et al. | 359/51 |
| 5,328,800 A | 7/1994 | Yokoya et al. | 430/203 |
| 5,330,264 A | 7/1994 | Ando et al. | 359/12 |
| 5,330,486 A | 7/1994 | Wilk | 606/139 |
| 5,354,498 A | 10/1994 | Akashi et al. | 252/299.01 |
| 5,356,557 A | 10/1994 | Jubb et al. | 252/299.01 |
| 5,363,228 A | 11/1994 | DeJule et al. | 359/117 |
| 5,366,462 A | 11/1994 | Kaster et al. | 505/153 |
| 5,376,095 A | 12/1994 | Ortiz | 505/143 |
| 5,377,008 A * | 12/1994 | Ridgway et al. | 356/481 |
| 5,384,067 A | 1/1995 | Doane et al. | 252/299.01 |
| 5,453,338 A | 9/1995 | Suga et al. | 430/1 |
| 5,471,326 A | 11/1995 | Hall et al. | 359/15 |
| 5,488,681 A | 1/1996 | Deacon et al. | 385/37 |
| 5,499,118 A | 3/1996 | Wreede et al. | 359/12 |
| 5,529,861 A | 6/1996 | Redfield | 430/1 |
| 5,544,268 A | 8/1996 | Bischel et al. | 385/4 |
| 5,547,786 A | 8/1996 | Brandstetter et al. | 430/1 |
| 5,593,615 A | 1/1997 | Nerad et al. | 252/299.01 |
| 5,641,426 A | 6/1997 | Nerad et al. | 252/299.01 |
| 5,648,857 A | 7/1997 | Ando et al. | 359/12 |
| 5,661,533 A | 8/1997 | Wu et al. | 349/169 |
| 5,661,577 A | 8/1997 | Jenkins et al. | 359/11 |
| 5,680,233 A | 10/1997 | Faris et al. | 359/41 |
| 5,682,214 A | 10/1997 | Amako et al. | 349/74 |
| 5,695,682 A | 12/1997 | Doane et al. | 252/299.01 |
| 5,698,134 A | 12/1997 | Jubb et al. | 252/299.01 |
| 5,698,343 A | 12/1997 | Sutherland et al. | 430/1 |
| 5,706,375 A | 1/1998 | Mihailov et al. | 385/24 |
| 5,725,970 A | 3/1998 | Martin et al. | 430/2 |
| 5,731,853 A | 3/1998 | Taketomi et al. | 349/15 |
| 5,734,485 A | 3/1998 | Buchkremer et al. | 359/25 |
| 5,748,272 A | 5/1998 | Tanaka et al. | 349/86 |
| 5,751,452 A | 5/1998 | Tanaka et al. | 359/52 |
| 5,771,320 A | 6/1998 | Stone | 385/16 |
| 5,832,148 A | 11/1998 | Yariv | 385/16 |
| 5,852,504 A | 12/1998 | Kato et al. | 359/9 |
| 5,862,214 A | 1/1999 | Aggus et al. | 379/435 |
| 5,864,641 A * | 1/1999 | Murphy et al. | 385/12 |
| 5,875,012 A | 2/1999 | Crawford et al. | 349/74 |
| 5,915,051 A | 6/1999 | Damask et al. | 385/16 |
| 5,917,607 A * | 6/1999 | Naya | 356/445 |
| 5,930,011 A | 7/1999 | Gambogi, Jr. et al. | 359/15 |
| 5,937,115 A | 8/1999 | Domash | 385/16 |
| 5,942,157 A | 8/1999 | Sutherland et al. | 252/582 |
| 5,989,923 A | 11/1999 | Lowe et al. | 436/518 |
| 6,115,152 A | 9/2000 | Popovich et al. | 359/15 |
| 6,130,748 A | 10/2000 | Kruger et al. | 356/345 |
| 6,172,778 B1 | 1/2001 | Reinhorn et al. | 359/15 |
| 6,187,599 B1 | 2/2001 | Asher et al. | 436/531 |
| 6,211,976 B1 | 4/2001 | Popovich et al. | 359/15 |
| 6,239,876 B1 * | 5/2001 | Brandenberg | 356/481 |
| 6,395,558 B1 | 5/2002 | Duveneck et al. | 436/172 |
| 6,493,090 B1 * | 12/2002 | Lading et al. | 356/484 |
| 6,689,316 B1 | 2/2004 | Blyth et al. | 422/56 |
| 6,723,516 B1 * | 4/2004 | Tom-Moy et al. | 435/7.1 |
| 6,771,857 B1 * | 8/2004 | Domash et al. | 385/37 |
| 6,781,696 B1 * | 8/2004 | Rosenberger et al. | 356/437 |
| 6,791,691 B2 * | 9/2004 | Ohtsuka et al. | 356/445 |
| 2001/0030741 A1 * | 10/2001 | Herron et al. | 356/39 |
| 2001/0040679 A1 | 11/2001 | Kawabata et al. | 356/445 |
| 2001/0044119 A1 | 11/2001 | Ghadiri et al. | 435/7.1 |
| 2002/0003627 A1 | 1/2002 | Rieder | 356/481 |
| 2003/0146109 A1 * | 8/2003 | Sailor et al. | 205/775 |
| 2004/0045932 A1 * | 3/2004 | Kochergin et al. | 216/59 |

FOREIGN PATENT DOCUMENTS

| | | |
|---|---|---|
| DE | 44 08 746 A1 | 9/1995 |
| EP | 0 087 281 A1 | 8/1983 |
| EP | 0 422 689 A2 | 4/1991 |
| EP | 0 672 386 A1 | 9/1995 |
| EP | 0 856 765 A1 | 8/1998 |
| EP | 0 856 766 A2 | 8/1998 |
| EP | 0 856 768 A2 | 8/1998 |
| EP | 0 867 749 A2 | 9/1998 |
| GB | 2 222 696 | 3/1990 |
| GB | 2 281 566 | 3/1995 |
| GB | 2 292 745 | 3/1996 |
| JP | 1-68784 A | 3/1989 |
| JP | 3-188479 A | 8/1991 |
| JP | 6-190185 | 4/1994 |
| JP | 10319237 | 12/1998 |
| SU | 1635966 | 3/1991 |
| WO | WO81/00668 | 3/1981 |
| WO | WO89/06264 | 7/1989 |
| WO | WO94/04958 | 3/1994 |
| WO | WO95/17127 | 6/1995 |
| WO | WO97/27519 | 7/1997 |
| WO | WO98/04650 | 2/1998 |

| | | | |
|---|---|---|---|
| WO | WO99/09440 | 2/1999 | |

OTHER PUBLICATIONS

International Search Report for Application No. PCT/US97/12577, dated Jan. 14, 1998 (mailing date).
Written Opinion for Application No. PCT/US97/12577, dated Apr. 28, 1998 (mailing date).
Preliminary Examination Report for Application No. PCT/US97/12577, dated Sep. 3, 1998 (mailing date).
European Search Report for Application No. EP 97 93 7988, dated Oct. 13, 1999.
International Search Report for Application No. PCT/US00/34661, dated Jul. 17, 2001.
International Preliminary Examination Report for Application No. PCT/US00/34661, dated Feb. 20, 2002.
International Search Report for Application No. PCT/US01/40691, dated Sep. 5, 2001 (mailing date).
Written Opinion for Appl. No. PCT/US01/4091, dated May 15, 2002 (mailing date).
Preliminary Examination Report for Appl. No. PCT/US01/40691, dated Sep. 10, 2002 (mailing date).
R. T. Pogue, et al., "Monomer Functionality Effects in the Anisotropic Phase Separation of Liquid Crystals," *Polymer* 41, pp. 733-741, 2000.
C. C. Bowley, et al., "Advances in Holographic Polymer Dispersed Liquid Crystal Technology," in *Liquid Crystal Materials and Devices*, Mat. Res. Soc. Symposium Proceedings, vol. 559, pp. 97-107, 1999.
C. C. Bowley, et al., "45.3: Electro-Optic Investigations of H-PDLCS: The Effect of Monomer Functionality on Display Performance," *SID International Symposium, Digest of Technical Papers*, First Edition, pp. 958-961, May 1999.
M. Date, et al., "Full-Color Reflective Display Device Using Holographically Fabricated Polymer-Dispersed Liquid Crystal (HPDLC)," *Journal of the Society for Information Disply(SID)*, vol. 7, pp. 17-22, 1999.
M. Escuti, et al., "5.3: A Model of the Fast-Switching Polymer-Stabilized IPS Configuration," *SID International Symposium, Digest of Technical Papers*, First Edition, pp. 32-35, May 1999.
Seferis, James C., "Refractive Indices of Polymers," *Polymer Handbook*, 4$^{th}$ Edition, John Wiley & Sons, Inc., pp. 571-582, Copyright 1999.
C. C. Bowley, et al., "Morphology of Holographically-Formed Polymer Dispersed Liquid Crystals (H-PDLC)," *Mol. Cryst. Liq. Cryst.*, vol. 331, pp. 209-216, 1999.
J. A. Firehammer, et al., "Lasing Pixels: A New Application for Polymer Dispersed Liquid Crystals (PDLCs)," *Mol. Cryst. Liq. Cryst.*, vol. 331, pp. 165-172, 1999.
Richard L. Sutherland, et al., "Switchable Holograms for Displays and Other Applications," *SPIE Proceedings*, vol. 3421, pp. 8-18, Jun. 1998.
L. V. Natarajan, et al., "Holographic PDLCs for Optical Beam Modulation, Deflection, and Dynamic Filter Applications," *SPIE Proceedings*, vol. 3292, pp. 44-51, Jan. 28-29, 1998.
K. Thilo Weitzel, et al., "Hologram Recording in DuPont Photopolymer Films by Use of Pulse Exposure," *Optics letter*, vol. 22, No. 24, Dec. 15, 1997.
L. V. Natarajan, et al., "Electrically Switchable Holograms Containing Novel PDLC Structures," *SPIE Proceedings*, vol. 3143, pp. 182-190, Jul. 28-29, 1997.
N. M. Lawandy, et al., "L1.3: Lasing Pixel PDLC Light Valves for Projection Applications," *SID International Symposium, Digest of Technical Papers*, First Edition, pp. 1001-1004, May 1997.
G. P. Crawford, et al., "Reflective Color LCDs Based on H-PDLC and PSCT Technologies," *Journal of the Society for Information Display*, vol. 5, No. 1, pp. 45-48, 1997.
J. Liu, et al., "Cross-Link Optimized Cascaded Volume Hologram Array with Energy-Equalized One-to-Many Surface-Normal Fan-Outs," *Optics Letters*, vol. 22, pp. 1024-1029 (1997).
V. N. Mikhailov, et al., "Pulse Hologram Recording in DuPont's Photopolymer Films," *SPIE*, vol. 3011, pp. 200-202, 1997.
D. Schwarze-Haller and F. Noack, "Nuclear Magnetic Resonance Field-Cycling Proton Relaxation Study of Polymer Dispersed Liquid Crystals," *J. Chem. Phys.*, vol. 105, No. 11, pp. 4823-4832, Sep. 1996.
G. P. Crawford, et al., "Reflective Color LCDs Based on H-PDLC and PSCT Technologies," *SID International Symposium, Digest of Applications Papers*, pp. 99, May 14-16, 1996.
Lawrence H. Domash, et al., "Switchable-Focus Lenses in Holographic Polymer Dispersed Liquid Crystal," *SPIE*, vol. 2689, pp. 188-194, May 1996.
Richard L. Sutherland, et al., "The Physics of Photopolymer-Liquid Crystal Composite Holographic Gratings," *SPIE Proceedings*, vol. 2689, pp. 158-169, May 1996.
T. J. Bunning, et al., "Liquid Crystals for Advanced Technologies," *Materials Research Society*, pp. 331-343, Apr. 8-11, 1996.
Timothy J. Bunning, et al., "The Effects of Eliminating the Chain Extender and Varying the Grating Periodicity on the Morphology of Holographically Written Bragg Gratings," *SPIE Proceedings*, vol. 2651, pp. 44-54, Jan. 31-Feb. 1, 1996.
T. J. Bunning, et al., "Morphology of Reflection Holograms Formed is situ Using Polymer-Dispersed Liquid Crystals," *Polymer*, vol. 37, No. 14, pp. 3147-3150, 1996.
G. S. Iannacchione, et al., "Deuterium NMR and Morphology Study of Polymer-Dispersed Liquid-Crystal Bragg Gratings," *Europhysics Letters*, vol. 36, No. 6, pp. 425-430, 1996.
L. V. Natarajan, et al., "Electro-Optical Switching Characteristics of Volume Holograms in Polymer Dispersed Liquid Crystals," *Journal of Nonlinear Optical Physics and Materials*, vol. 5, No. 1, pp. 89-98, Jan. 1996.
R. L. Sutherland, et al., "Switchable Bragg Gratings Formed in situ Within a Polymer-Dispersed Liquid Crystal Composite Medium," *Materials Research Society Symp. Proc.*, vol. 425, pp. 331-341, Apr. 8-11, 1996.
Richard L. Sutherland, et al., "Analysis of Periodic Polymer-Dispersed Liquid Crystal Structures for Dynamic Hologram Applications," *SPIE Proceedings*, vol. 2532, pp. 309-318, Jul. 10-12, 1995.
V. P. Tondiglia, et al., "Volume Holographic Image Storage and Electro-Optical Readout in a Polymer-Dispersed Liquid Crystal Film," *Optics Letters*, vol. 20, No. 11, pp. 1325-1327, Jun. 1, 1995.
Richard L. Sutherland, et al., "Switchable Holograms in New Photopolymer-Liquid Crystal Composite Materials," *SPIE Proceedings*, vol. 2404, pp. 132-143, Feb. 9-10, 1995.
N. Kawatsuki and H. Ono, "Electro-Optical Properties of Polymer/(Liquid Crystal) Composite Film Fabricated by Two-Step Phase Separation Method," *Chemistry Letters*, No. 5, pp. 333-334, 1995.
T. J. Bunning, et al., "The Morphology and Performance of Holographic Transmission Grating Recorded in Polymer Dispersed Liquid Crystals," *Polymer*, vol. 36, No. 14, pp. 2699-2708, 1995.
R. L. Sutherland, et al., "Electrically Switchable Volume Gratings in Polymer-Dispersed Liquid Crystals," *Appl. Phys. Lett.*, vol. 64, No. 9, pp. 1074-1076, Feb. 28, 1994.
Richard L. Sutherland, et al., "Development of Photopolymer-Liquid Crystal Composite Materials for Dynamic Hologram Applications," *SPIE Proceedings*, vol. 2152, pp. 303-313, Jan. 26-28, 1994.
J. Zhang, et al., "Switchable Holograms Recorded in Liquid Crystalline Monomers," *SPIE*, vol. 2042, pp. 238-247 (Jan. 1994).
K. Tanaka, et al., "Holographically Formed Liquid-Crystal/Polymer Device for Reflective Color Display," *Journal of the Society for Information Display*, vol. 2, No. 1, pp. 37-38, 1994.
L. Domash, et al., "Programmable Beamlet Generator, Dynamic Lens, and Optical Memory Using Electrically Swtiched Holographic Devices," *SPIE Proceedings*, vol. 2026, pp. 642-652, Nov. 1993.
D. J. Lougnot, et al., "Photopolymers for Holographic Recording: IV. New Self-Processing Formulations Based on β Hydroxy Ethyloxazolidone Acrylate," *Pure Appl. Opt.*, vol. 2, pp. 383-392, 1993.
R. L. Sutherland, et al., "Bragg Gratings in an Acrylate Polymer Consisting of Periodic Polymer-Dispersed Liquid Crystal Planes," *Chem. Mater.*, vol. 5, No. 10, pp. 1533-1538, 1993.
H. I. Bjelkhagen, et al., "High-Resolution Contact Denisyuk Holography," *Applied Optics*, vol. 31, No. 8, pp. 1041-1047, Mar. 10, 1992.

Hideya Murai, et al., "Electro-Optic Properties for Liquid Crystal Phase Gratings," *SPIE Proceedings,* vol. 1665, pp. 230-239, Feb. 11-13, 1992.

Lawrence H. Domash, "Applications of Dynamic Holograms for Quasi-Volume Storage," *SPIE Proceedings, Very Large Optical Memories-Materials and System Architectures,* vol. 1773, 5 pp., 1992.

J. Zhang, et al., "Switchable Liquid Crystalline Photopolymer Media for Holography," *J. Am. Chem. Soc.,* vol. 114(4), pp. 1506-1507 (1992).

Richard T. Ingwall and Timothy Adams, Hologram: Liquid Crystal Composites, *SPIE Proceedings,* vol. 1555, pp. 279-290, Jul. 24-25, 1991.

R. L. Sutherland, "Optical Limiters, Switches, and Filters Based on Polymer Dispersed Liquid Crystals," *SPIE Proceedings,* vol. 1080, pp. 83-90, Jan. 17-18, 1989.

A. M. Lackner, et al., "Droplet Size Control in Polymer Dispersed Liquid Crystal Films," *SPIE Proceedings,* vol. 1080, pp. 53-61, Jan. 17-18, 1989.

Yariv, Amnon, "Quantum Electronics, Third Edition," *John Wiley & Sons,* Copyright 1989, pp. 608-614.

G. von Bally, et al., "Gradient-Index Optical Systems in Holographic Endoscopy," *Applied Optics,* vol. 23, No. 11, pp. 1725-1729, Jun. 1, 1984.

Allan R. Tokuda, et al., "Holocamera for 3-D Micrography of the Alert Human Eye," *Applied Optics,* vol. 19, No. 13, pp. 2219-2225, Jul. 1, 1980.

Stephen A. Benton, et al., "One-Step White-Light Transmission Holography," *SPIE,* vol. 215, pp. 156-161, 1980.

Stephen A. Benton, et al., "One-Step White-Light Transmission Holography," *SPIE,* vol. 212, pp. 2-7, 1979.

Hori, Asai, and Fukai, "Field-Controllable Liquid-Crystal Phase Grating," *IEEE,* vol. ED-16, p. 1734 (4 pp.), 1979.

Born and Wolf, "Principles of Optics," $5^{th}$ Edition, New York (1975).

R. A. Kashnow and J. E. Bigelow, "Diffraction From a Liquid Crystal Phase Grating," *Applied Optics,* vol. 12, No. 10, pp. 2302-2304, Oct. 1973.

Stoke, Funkhouser, Leonard, Indebetoew, and Zech, "Hand-Held Holography," 1 p., Sep. 19, 1966.

G. W. Stroke and A. E. Labeyrie, "White-Light Reconstruction of Holographic Images Using the Lippmann-Bragg Diffraction Effect," *Physics Letters,* vol. 20, No. 4, pp. 368-370, Mar. 1, 1966.

Edited by H. Bennett, "Cooncise Chemical and Technical Dictionary, FAIC," Chemical Publishing Co., Inc., 1974.

* cited by examiner

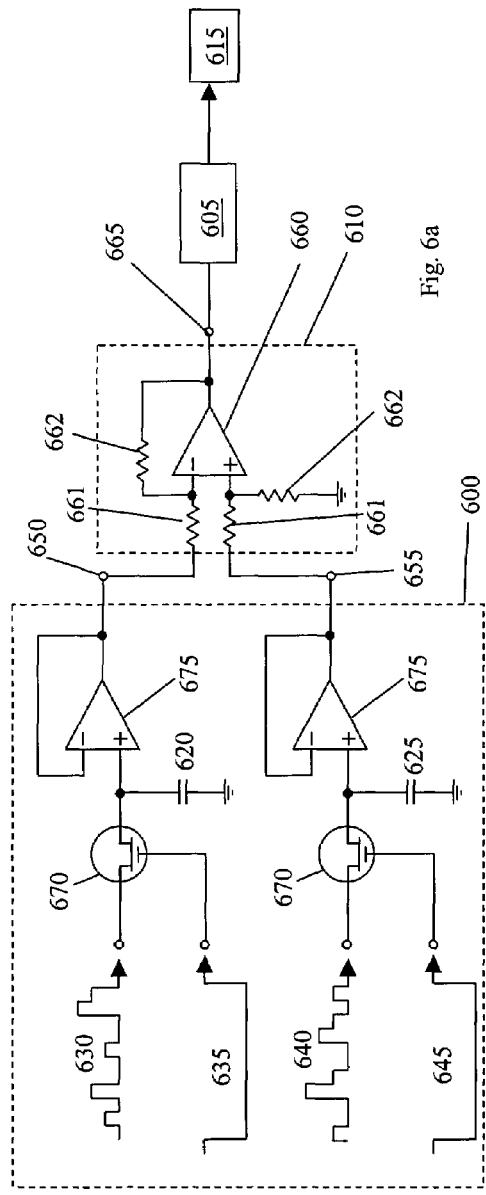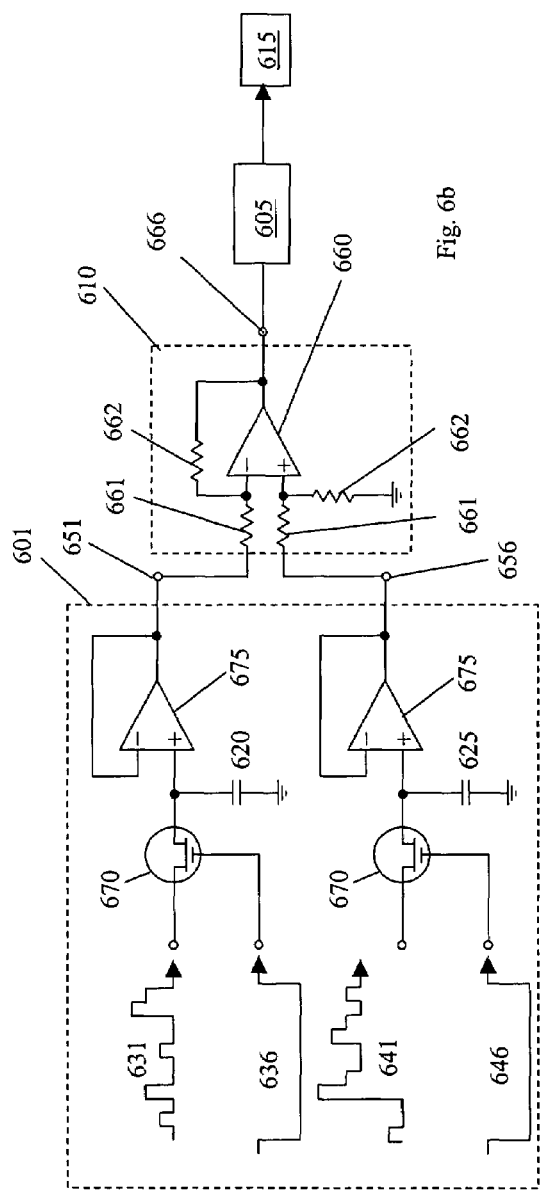

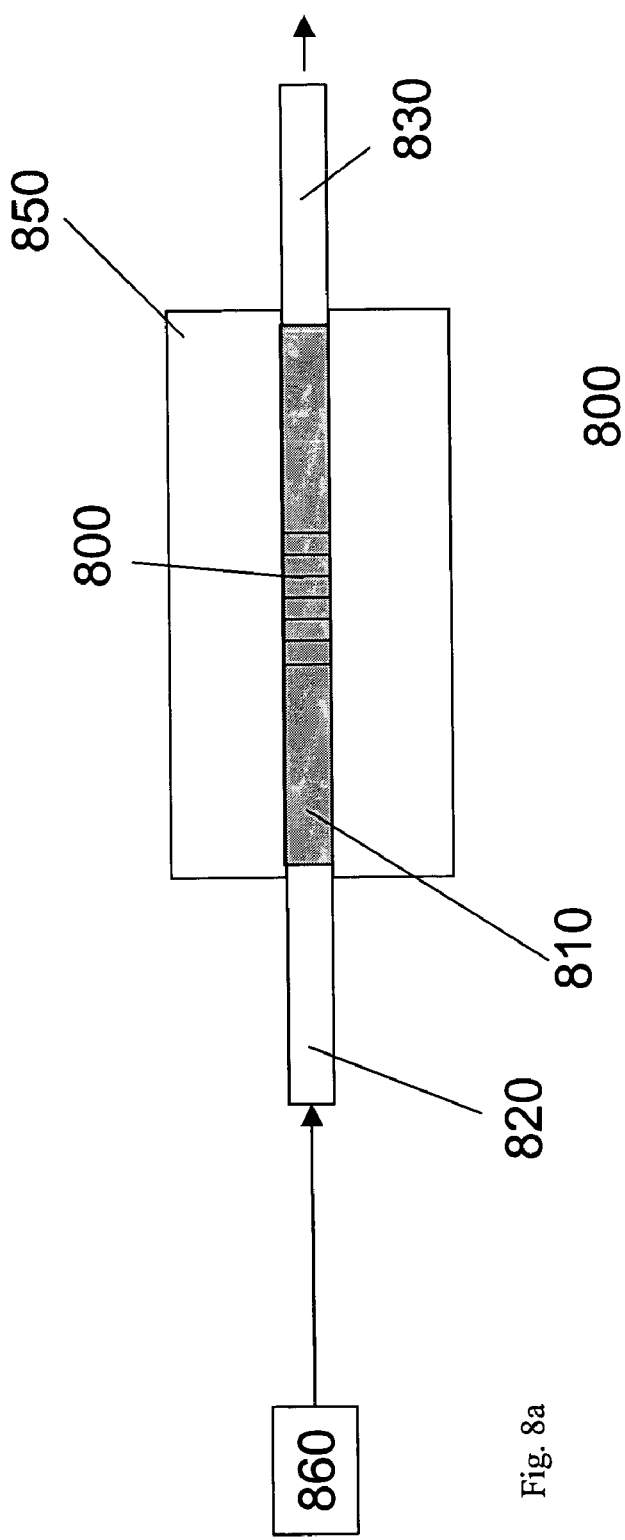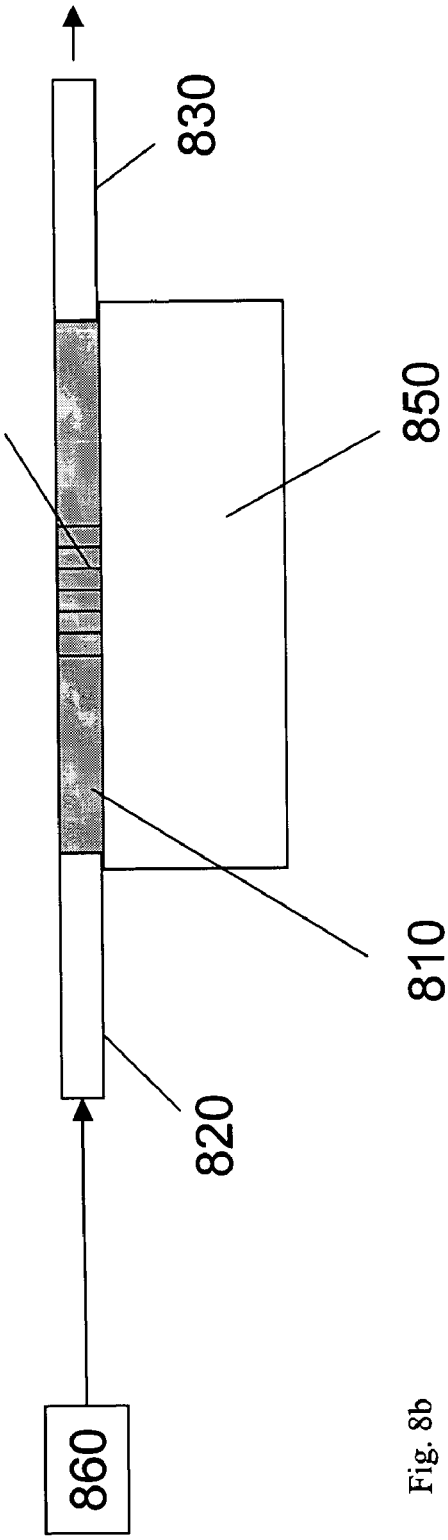
Fig. 8a
Fig. 8b

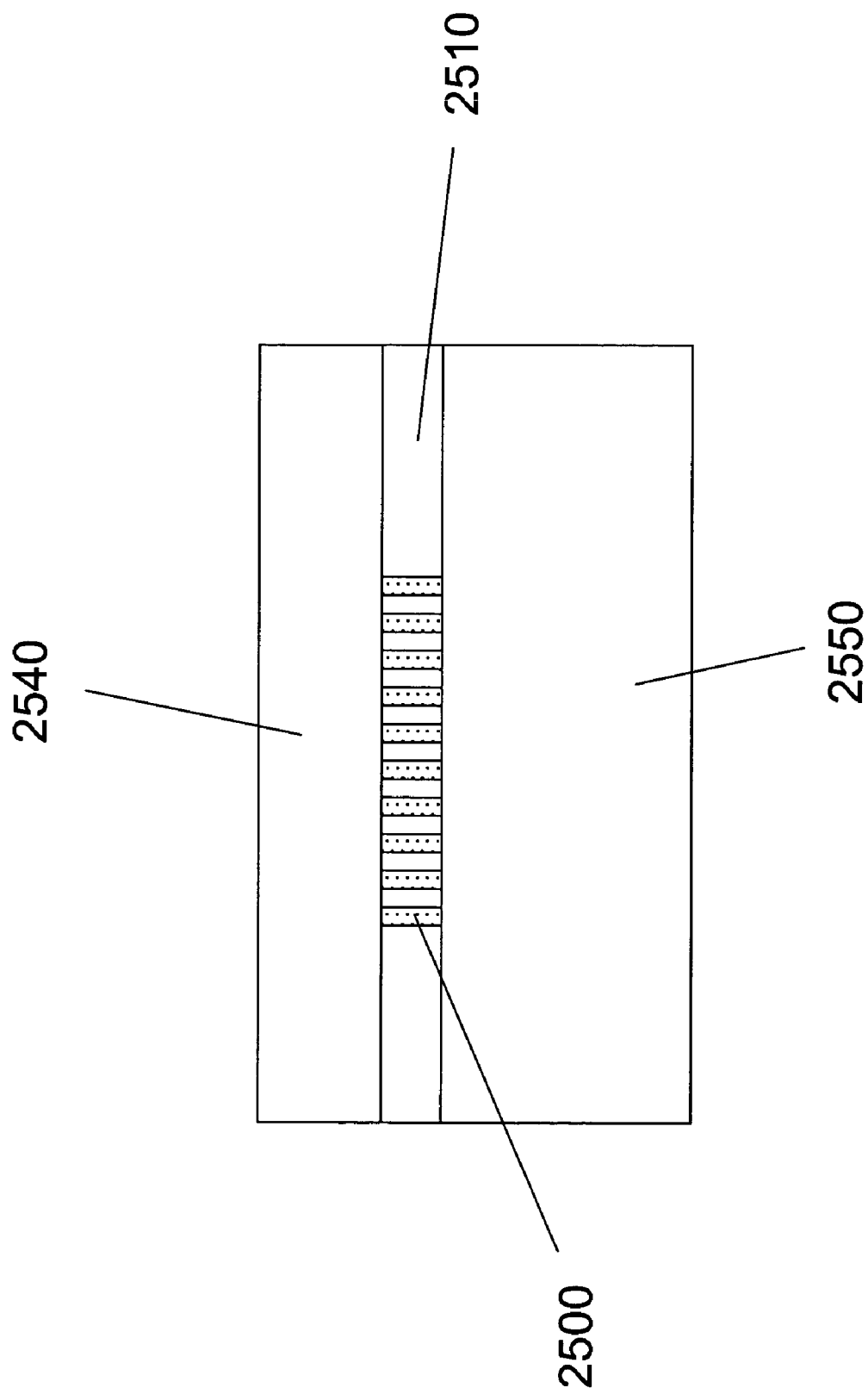

DETECTION AND IDENTIFICATION OF BIOLOGICAL AGENTS USING BRAGG FILTERS

CROSS-REFERENCE TO RELATED APPLICATIONS

This application claims priority to and incorporates by reference in its entirety U.S. Provisional Patent Application No. 60/406,665 entitled "METHOD AND APPARATUS FOR DETECTION AND ANALYSIS" filed Aug. 29, 2002.

BACKGROUND OF THE INVENTION

1. Field of the Invention

The present invention relates generally to a sensor system, and more specifically to a sensor for detecting biological and chemical agents in the environment.

2. Description of the Related Art

Antibody-based detection systems are the most mature and advanced technology for biological agent detection and identification. Antibodies are defined as any of the body immunoglobulins that are produced in response to specific antigens and that counteract their effects by neutralizing toxins, agglutinating bacteria or cells, and precipitating soluble antigens. Antigens are defined as protein or carbohydrate substances capable of stimulating an immune response. Antibodies are very specific and bind only to their target, even in the presence of other material. In a detector, antibodies are normally immobilized on a substrate, e.g., a polymer, such as polyvinylethylene, polyethylene, or polystyrene, for subsequent incubation with the target organism or molecule. Typically, the antibodies are not chemically bound to the substrate, but merely attached by hydrogen bonding or electrostatic charge. The antibody and antigen bind upon contact, thereby immobilizing the antigen. Classically, a second antibody to the target agent incubates, as well as binds to the antigen. This second antibody is generally linked to some type of reporter system, usually an enzyme. The varying forms of these reporter systems include, e.g., fluorescent, magnetic, enzymatic, calorimetric, etc. This transducer provides the means of detecting the presence of the antigen of interest. Enzyme linked immunosorbent assay (ELISA) is based on this process.

An analyte in the antibody-antigen detection system is typically in an aqueous solution or other liquid solution. The aqueous solution must make frequent and intimate contact with the immobilized antibody on the substrate material. A large surface area on the substrate allows a higher density of antibodies and hence a higher sensitivity. However, the antibodies must be tightly bound to the substrate to survive repeated motion of the analyte over the substrate without becoming detached and flushed away with the solution. Therefore, covalent bonding, rather than hydrogen bonding or electrostatic bonding, of the antibodies to the substrate is preferential. Many biological compounds of interest in the system are proteins, e.g., enzymes, hormones, toxins, antibodies, and antigens. Proteins are composed of amino acids, having both an amino group ($NH_2$) and a carboxylic acid group (COOH). A substrate functionalized with one or both of these groups can be activated to chemically bind antibodies.

The introduction of a second antibody in the ELISA process complicates and slows down the detection/identification process. A physical property change produced by the antibody-antigen chemical reaction provides the basis for a more direct transduction mechanism. The transduction mechanism in an optics-based detection system is based on a change in absorption or index of refraction, which is monitored by the optical system.

Several detectors are based on a change of index of refraction. One such sensor is based on surface plasmon resonance. Surface plasmon techniques are difficult to integrate for multiplexed operation where multiple target agents can be monitored simultaneously. Also, their sensitivity cannot be engineered by sharpening the spectral or angular response to light.

Other known sensors include a chemical sensor based on porous silicon and a porous-semiconductor-based, e.g., porous Si, optical interferometric sensor. Interference filters can be made with porous silicon. However, porous silicon interference filters are incompatible with polymer waveguide technology and hence cannot be readily integrated onto a polymer waveguide chip. Also, porous polymers are easier to apodize, i.e., sharpen, their spectral response using holographic techniques. Moreover, polymer chemistry is more adaptable to functionalization with chemical groups for binding antibodies and antigens. Most immunosorbent assays are conducted on polymer substrates. Porous silicon has not been widely used for this application. No conventional methods propose the simultaneous use of porous semiconductors as both chemical and optical filters.

Another known sensor is a doubly-differential interferometer-based sensor with evanescent wave surface detection. This sensor is a surface detector only and cannot take advantage of the extended surface area of a porous polymer. Furthermore, the sensor also requires polarized light and a modulator. Additionally, this sensor is a part of a system that does not provide for continuously monitoring the environment. The interferometer is also not flexible for sharpening the optical response for higher sensitivity.

Another sensor, in the form of polymerized crystalline colloidal arrays, achieves detection of chemical and biological agents by a change in diffraction accompanying the swelling or shrinkage of a hydrogel containing the crystalline colloidal array in response to a chemical reaction with target agent(s). Similarly, a conventional hologram-containing sensor consists of a holographic grating recorded preferably in a gelatin, where reaction of chemical agents with the gelatin produces some change in the physical properties of the hologram matrix, thereby changing the diffraction properties of the hologram. In both the polymerized crystalline arrays and the hologram-containing sensor, a matrix containing a grating serves to uptake an analyte, but does not allow for the analyte to flow through the system. Once the system is swollen, the only mechanism for replacing it with new samples is to remove the grating from the system and dry it out. Since the materials used are not porous, the system cannot take advantage of increased surface area to volume ratio and does not provide a convenient method for chemically filtering the analyte. These methods are also not compatible with waveguides for integration onto a chip.

Another chemical and biochemical sensor includes a planar waveguide with a grating coupler. A recognition layer containing specific chemical or biochemical binding partners, e.g., antibodies or antigens, is located on the waveguide. A chemical reaction on the recognition layer changes the effective refractive index of the guiding layer, thereby changing the coupling efficiency of the grating, i.e., the angle of incidence for maximum input coupling to the waveguide. Using this sensor, a method for optical determination of an analyte records the position of light points with a position sensitive detection method. The grating is a surface grating formed by standard methods, i.e., photolithographic patterning followed by etching. A surface grating sensor cannot take advantage of the extended surface area of a porous polymer, since the grating cannot be extended throughout the volume of the porous polymer and chemical detector or recognition molecules cannot be dispersed throughout the volume to increase its chemical sensitivity. This system does not provide a mechanism for continuously monitoring the environment by flowing the analyte through the grating, since it is only a surface grating. Nor does the system use the grating as an optical filter to take advantage of the sharp spectral properties of a Bragg grating for detecting large changes in transmission of such a filter with relatively small changes in refractive index.

SUMMARY OF THE INVENTION

Summary of the Problem:

The rapid detection and identification of hazardous biological and chemical agents has become an increasing concern due to the dangers of biological and chemical warfare as well as the threat of terrorists releasing such agents in public venues. Before troops are deployed in forward staging areas, biosensors need to assess the environment for force protection. In terrorist situations, adequate security measures require continuous monitoring of high value public areas, such as government buildings, subways, stadiums, water treatment plants, etc. First responders to a biological or chemical terrorist attack need to quickly and accurately detect and identify the particular biological or chemical agent to take necessary precautions and adequately administer aid. Although standoff sensors, such as lidar, provide some remote sensing of the release of agents, they cannot identify particular agents. Point detection systems can sense the immediate environment. Specificity is a necessary ingredient in the sensor system. Compact, rugged, reliable sensor systems that can continuously monitor the environment are desired. With appropriate telemetry systems, these can be deployed in forward battle areas during warfare (for example, delivered by drones or dropped by parachute) or placed in high value public areas to continuously monitor and report environmental changes that may indicate a terrorist attack.

Conventional means of detecting biological agents in the environment, e.g., laser induced fluorescence, accurately detect the presence of biological agents. These detectors do not, however, provide the specificity to identify the agents present. Additionally, these devices are complex and bulky. Other devices capable of agent detection and identification, e.g., mass spectrometry, are expensive and not easily portable. These devices take a considerable amount of time to identify the agent(s). Still other devices, utilizing immunoassay techniques, identify agents with high specificity by antigen-antibody chemical reactions. Unfortunately, these techniques are not readily amenable to providing continuous, always-on monitoring of the environment. Moreover, these techniques are not reagentless; they normally require additional chemistry to add chromophores or fluorescing agents for detection and identification by color change or fluorescence. A need exists for a compact, inexpensive, portable biosensor system that can continuously monitor the environment, i.e., always-on mode, and both detect and identify biological agents in the environment with high specificity and a low false alarm rate.

Summary of the Solution:

The conventional methods neither achieve nor teach methods or devices to meet the above-mentioned criteria for a biosensor. Therefore, it is an object of this invention to provide a compact, inexpensive, rugged and portable biosensor that can continuously monitor the environment for detection and identification of hazardous biological agents.

The solution to the conventional methods is to continuously monitor the environment for hazardous biological and biochemical agents, providing rapid, automatic, simultaneous detection and identification of such agents with high specificity and low false alarm rate. Such a system continuously draw samples from the environment, i.e., air, water, or soil, for analysis. The system repeatedly and indefinitely exposes the detector to the samples. The detector specifically recognizes the target agents and responds by some physical or chemical change of state. Based on the change in the detector state, a transduction mechanism produces a useable signal. The detection mechanism is highly sensitive, achieving a rapid response with low probability of false signals, whether positive or negative indications. The detector is rugged and can reliably respond even after being subjected to multiple sample exposures. The system provides a platform insusceptible to external temperature swings and vibrations.

It is furthermore an object of this invention to monitor air and/or water and/or soil continuously for the detection and/or identification of hazardous biological agents.

It is furthermore an object of this invention to provide a working fluid that is continuously circulated in the sensor as a medium for transporting environmental samples to detector modules for always-on monitoring of the presence of hazardous biological agents.

It is furthermore an object of this invention to provide a detector consisting of a porous polymer Bragg grating that functions simultaneously as a chemical filter, to trap specific target agents for detection by a highly specific chemical reaction with a conjugate molecule, and as an optical filter that provides the transduction mechanism to create a measurable signal stemming from the chemical reaction.

It is furthermore an object of this invention to provide a detector consisting of a porous polymer Bragg grating that has a high surface area to volume ratio to provide a high density of binder molecules that increases the probability of target agent binding and hence increases the detection sensitivity.

It is furthermore an object of this invention to provide a detector consisting of a porous polymer Bragg grating that can be fabricated holographically as a thick filter with low index modulation, hence achieving a sharp spectral transmission or reflection notch that enhances the detection sensitivity.

It is furthermore an object of this invention to provide a detector consisting of a porous polymer Bragg grating that can be fabricated holographically to apodize the filter, sharpen the spectral response and enhance the detection sensitivity.

It is furthermore an object of this invention to provide an array of detector modules consisting of porous polymer Bragg gratings, each of which is sensitized with a different molecule for binding specific target agents and can hence monitor the presence of multiple hazardous biological agents in the environment.

It is furthermore an object of this invention to provide an array of detector modules consisting of porous polymer Bragg gratings, where each module consists of more than one detector arm having said porous polymer Bragg gratings, and only one arm is sensitized with a particular detector molecule, the other arm(s) serving as control and reference that factor out the effects of thermal and light source fluctuations and drift, or other environmental disturbances, and factor out transient effects from inert microscopic material contained in the environmental sample, thereby achieving a low false alarm rate.

It is furthermore an object of this invention to provide a system that does not require additional chemistry to add chromophores or fluorescing agents for detection and identification by color change or fluorescence.

It is furthermore an object of this invention to provide detection sensitivity by combined optical and electronic differential gain.

It is furthermore an object of this invention to provide a sensor capable of rapid response due to high detection sensitivity.

A first embodiment of the present invention describes a method of determining a target agent in an environment comprising the steps of obtaining a first sample from the environment and introducing the first sample to at least one detection module. The first sample is then filtered through at least a first filter and a second filter comprising at least one detection module, wherein the first filter contains at least one detection molecule for the target agent and the second filter contains no detection molecules for the target agent. An optical property is measured from the first filter and the second filter after filtering the first sample there through. Comparing the measured optical property of the first filter to the measured optical property of the second filter assists in determining the presence of the target agent.

A second embodiment of the present invention describes a sensor for determining the presence of at least one target agent in a sample comprising a collector system for collecting the sample from an environment, a transfer system for adding the sample to a working fluid, a dispenser system for introducing the working fluid, including the sample, to a detector system, and a detector system comprising at least one detector module. The detector module includes at least a first optical grating and a second optical grating, wherein the first optical grating contains at least one detector molecule for detecting the at least one target agent and the second optical grating does not contain a detector molecule for detecting the at least one target agent. The detector module further includes at least a first measuring device for measuring an optical response of the first optical grating after contact with the working fluid, including the sample, and at least a second measuring device for measuring an optical response of the second optical grating after contact with the working fluid, including the sample. A processor compares the measured optical response from the at least a first measuring device to the measured optical response from the at least a second measuring device to determine the presence of the target agent.

A third embodiment of the present invention describes a detector module for detecting a target agent within a sample comprising at least one inlet reservoir for receiving the sample therein, a first micro-fluidic channel integrally connected to the at least one inlet reservoir, a second micro-fluidic channel integrally connected to the at least one inlet reservoir, a first optical grating physically integrated with the first micro-fluidic channel and a second optical grating physically integrated with the second micro-fluidic channel, wherein the first optical grating includes at least one detector molecule for detecting the target agent within the sample and the second optical grating does not include a detector molecule for detecting the target agent within the sample. The detector module also comprises at least one outlet reservoir physically integrated with the first micro-fluidic channel for removing the sample from the detector module.

A fourth embodiment of the present invention describes a method for forming an optical sensor for sensing the presence of a target agent in a sample comprising interfering a first coherent beam and a second coherent beam within a polymerizable polymer-dispersed liquid crystal material forming a polymerized hologram containing liquid crystals within a polymer matrix. The liquid crystals are extracted from the polymer matrix forming pores therein. The binding sites within the pores are chemically activated for receipt of a detector molecule therein. A detector molecule is attached within the pores for sensing the presence of a target agent in a sample.

BRIEF DESCRIPTION OF THE FIGURES

The present invention will be more clearly understood from a reading of the following description in conjunction with the accompanying figures wherein:

FIGS. 6a and 6b show electronic processing according to an embodiment of the present invention;

FIGS. 8a and 8b show a grating in a waveguide according to an embodiment of the present invention;

FIG. 25 shows a grating situated in a waveguide according to an embodiment of the present invention.

DETAILED DESCRIPTION OF THE PREFERRED EMBODIMENTS OF THE PRESENT INVENTION

Figure 1:
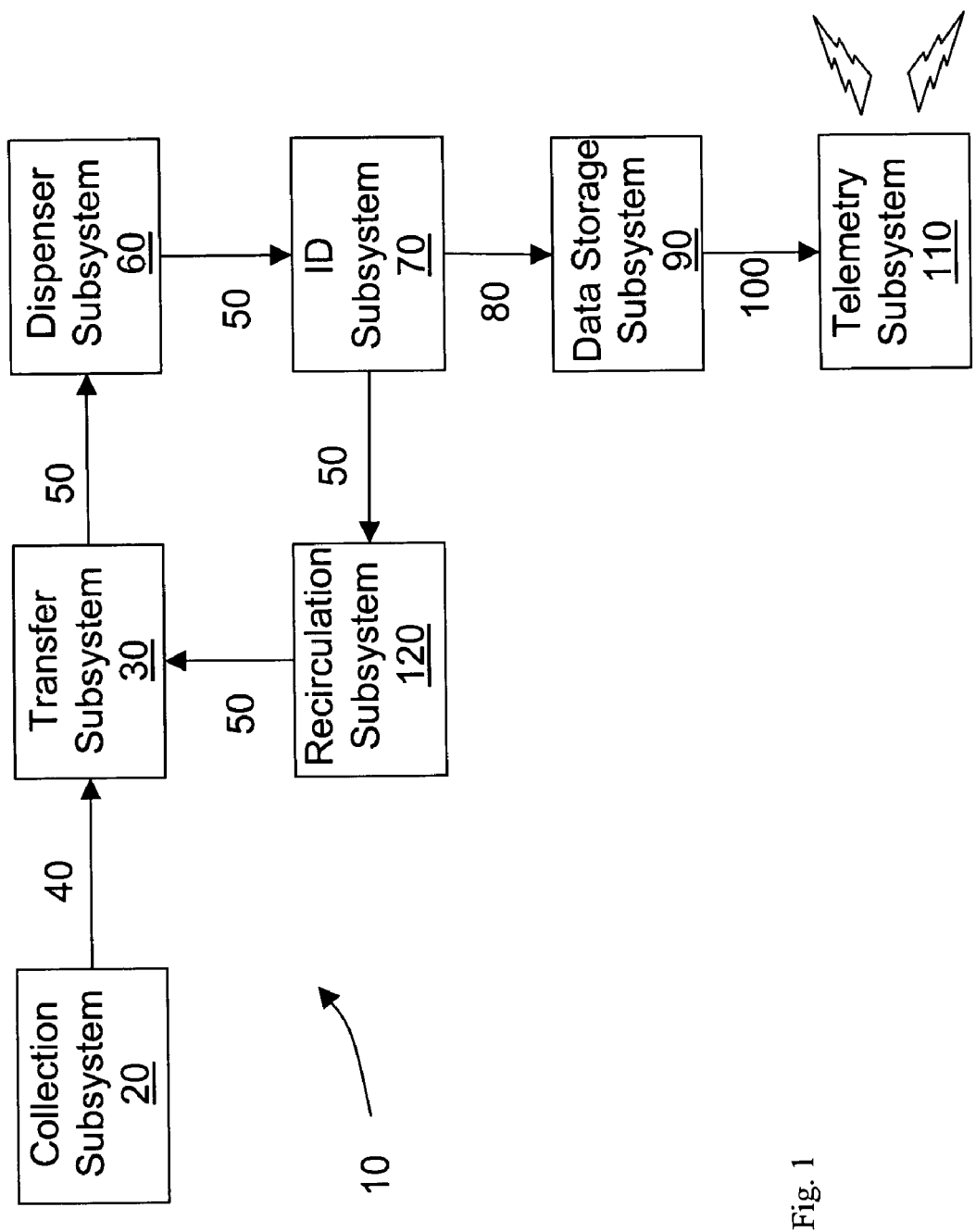
FIG. 1 shows a detection system according to an embodiment of the present invention.
Figure 2:
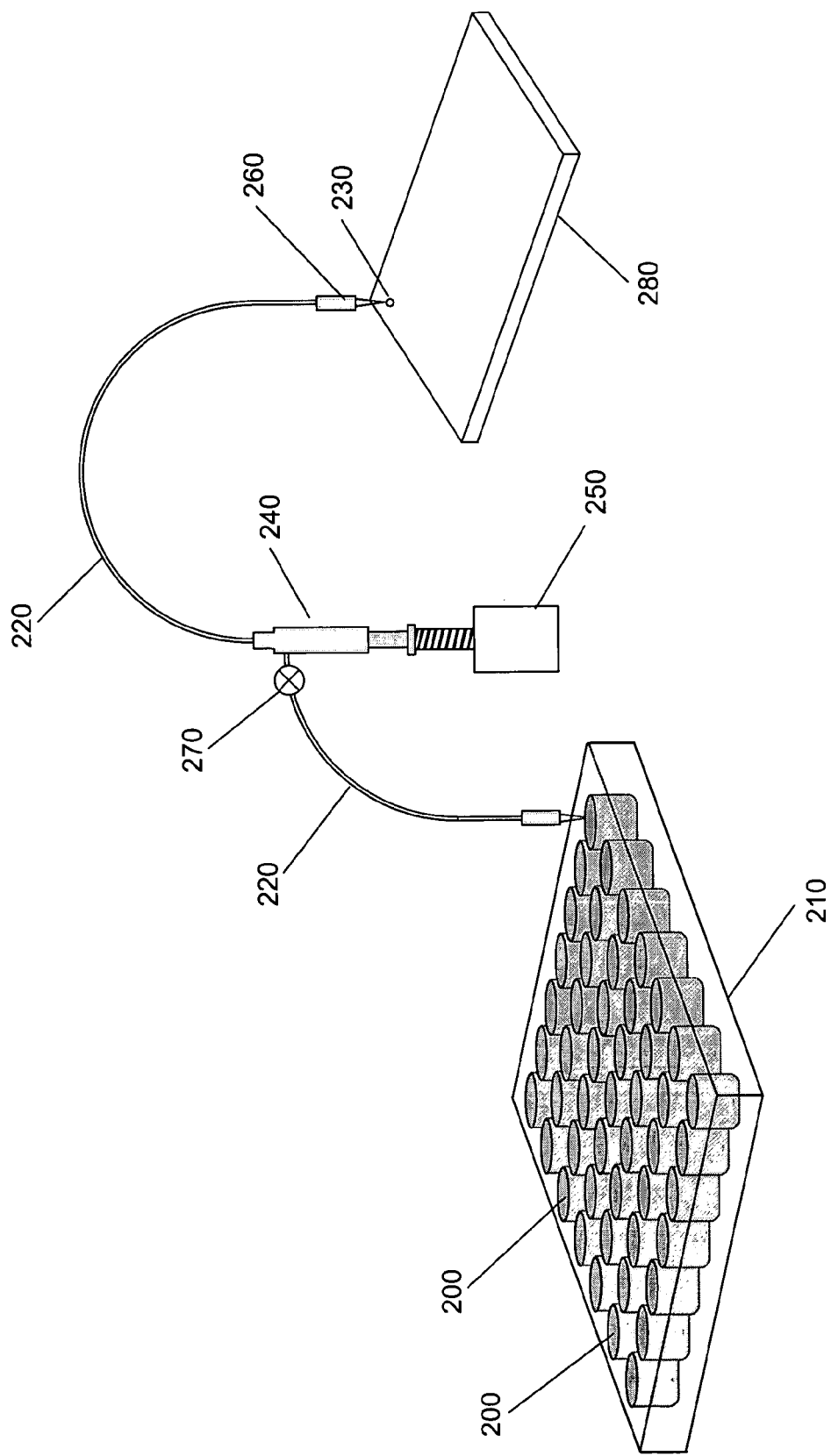
FIG. 2 shows a subsystem of a detection system according to an embodiment of the present invention.

In an embodiment of the present invention as shown in FIG. 1, a biological and chemical target agent sensor 10 has a sample collection subsystem 20 that continuously draws samples of air, water, and soil from the environment. A transfer subsystem 30 transfers the sample 40 from the collection subsystem 20 to working fluid 50. A dispenser subsystem 60 dispenses the working fluid 50 containing the sample into a detector module array ("DMA") of a detection/identification (hereafter "ID") subsystem 70.

The dual-function ID subsystem 70 sends the sample data from the DMA through an electronic signal 80 to a data storage subsystem 90. Data storage subsystem 90 obtains and continuously compiles data from the DMA. The data within data storage subsystem 90 may either be accessed directly or may be sent via an appropriate transmission system, such as telemetry subsystem 110, for recording and analysis. The transmission system may send data at pre-selected intervals in batch format or, alternatively, may send data on a continual basis. Further still, the data storage system 90 may perform analysis on the data from the ID subsystem 70 prior to forwarding for transmission. With this embodiment, the data storage subsystem 90 may be programmed to transmit data when a particular result is found, e.g., a target agent has been identified.

As a second function, after passing through the ID subsystem 70, the working fluid 50 is transferred to a recirculation subsystem 120. Recirculation subsystem 120 decontaminates the working fluid 50 and returns the working fluid 50 to the transfer subsystem 30 to obtain another environmental sample. The recirculation subsystem 120 consists of an ultrafine filter and an ultraviolet lamp that destroys/removes foreign material remaining in the working fluid. The working fluid is passed through micro-tubing and a low-flow pump. The working fluid then returns to the transfer subsystem 30 to pick up another sample 40 of the environment. The constant sampling and recirculation allows the system to continuously monitor the environment. In essence, it is "always on."

At the onset of the system of sensor 10, collection subsystem 20 has an air sampler, preferably consisting of a pump for drawing through air from the environment, a horn or similar instrument for directing the air flow, a filter stage consisting of one or more filters to remove large particles, e.g., greater than 10 μm, and an exhaust system. For sampling gases and aerosols in the air, the collection subsystem 20 is adapted from conventional air samplers such as those provided by Airmetrics, Mattson-Garvin, SKC, or Sceptor Industries. For sampling water, e.g., standing water, wastewater, etc., the collection subsystem 20 is adapted from conventional water samplers such as the Markland Duckbill® Sampling System, or an equivalent supplied by such companies as Global Water Instrumentation, Inc., and others. In one embodiment, the water sampler consists of a remote sampler head submerged in the water or a tube submerged in the water. A sampler pump/controller draws water samples through a filter stage to remove large particles, e.g., greater than 10 μm. The water sample is then retained in a holding container for transfer of microscopic agents to the working fluid. The water is then flushed out of the system to make room for the next sample. For sampling soil, the collection subsystem 20 is adapted from conventional soil water samplers such as those supplied by Soil Monitoring Engineering. Soil water samplers, such as lysimeters or porous ceramic cups, are buried in the soil. A pump creates a partial vacuum, which causes water in the surrounding soil to enter the sampler via a porous ceramic filter. The sample is then retained in a holding container for transfer of microscopic agents to the working fluid. The water is then flushed out of the system to make room for the next sample.

The environmental samples are transferred to a working fluid by a transfer subsystem 30. The transfer subsystem 30 transfers potentially hazardous microscopic agents, as well as other microscopic constituents, from the environment to working fluid 50 of the sensor 10. Transfer subsystem 30 may be adapted from conventional products. For gas/water transfers, the transfer subsystem 30 is adapted from conventional gas bubblers, such as those supplied by SKC. The air sample is bubbled through the working fluid, and gases from the atmosphere are dissolved in the fluid. For aerosol/water transfers, the transfer subsystem 30 is adapted from conventional particle impingers, such as those supplied by SKC. Aerosol particles impinge on the working fluid and become trapped in the liquid. For water/water transfers, the transfer subsystem 30 is adapted from conventional dialysis cells, such as the DMLS™ supplied by Margan. The gradient of concentrations allows for material dissolved in the environmental water to diffuse into the working fluid 50 contained in the dialysis cell.

The working fluid 50 is typically an aqueous solution compatible with the molecular detectors. The working fluid 50 continuously flows through the system to provide an always-on monitoring device. Although the working fluid 50 necessarily comes into contact with the environment, it must be held at a constant temperature and appropriate chemical composition, e.g., pH, to optimize the sensor 10 and enhance the lifetime of the complex detector molecules, e.g., antibody proteins. A heater or a thermoelectric cooler system controls the temperature of the working fluid for optimum operation of about 30-40° C.

Dispenser subsystem 60 receives the working fluid from transfer subsystem 30. Referring to FIG. 1, dispenser subsystem 60 dispenses working fluid 50, containing the microscopic environmental samples, to ID subsystem 70 comprising a multi-channel DMA. Further to dispenser subsystem 60, a mixer mechanically agitates the working fluid 50 to form a homogenous mixture of agents throughout the volume of the working fluid 50. This ensures that when the working fluid passes from the dispenser 60 to the ID subsystem 70, each channel of the DMA monitors identical samples. After passing through a filter to separate out larger particles (e.g., greater than 1 μm or greater than 0.1 μm, depending on filter selection), the working fluid 50 then passes to an array of micro-wells. Each micro-well of the micro-well array is capable of holding approximately 1 μL of working fluid. Referring to FIG. 2, from each of the micro-wells 200, one of an array of syringes 240 draws a carefully metered volume of working fluid 230, e.g., by use of a stepper motor 250. A valve 270 is then closed, and the syringe 240 dispenses the working fluid 230 via micro-tubing 220 to a micro-pipette 260. Since the porous polymer Bragg grating absorbs approximately 10-100 nL of fluid at a time, the micro-tubing 220 delivering the working fluid 230 to the micro-pipette fluid dispensers 260 may be similarly sized to catheter tubes. The micro-pipette fluid dispensers 260 hold approximately 1 μL of fluid and are capable of accurately dispensing approximately 10-100 nL of working fluid. The micro-pipette fluid dispensers 260 dispense the solution to the detector modules 280 of the DMA for identification of a target agent. The number of micro-wells 200 and fluid dispensers 260 in the array 210 range in size from at least one to hundreds, depending on the number of agents that need to be monitored.

Figure 3:
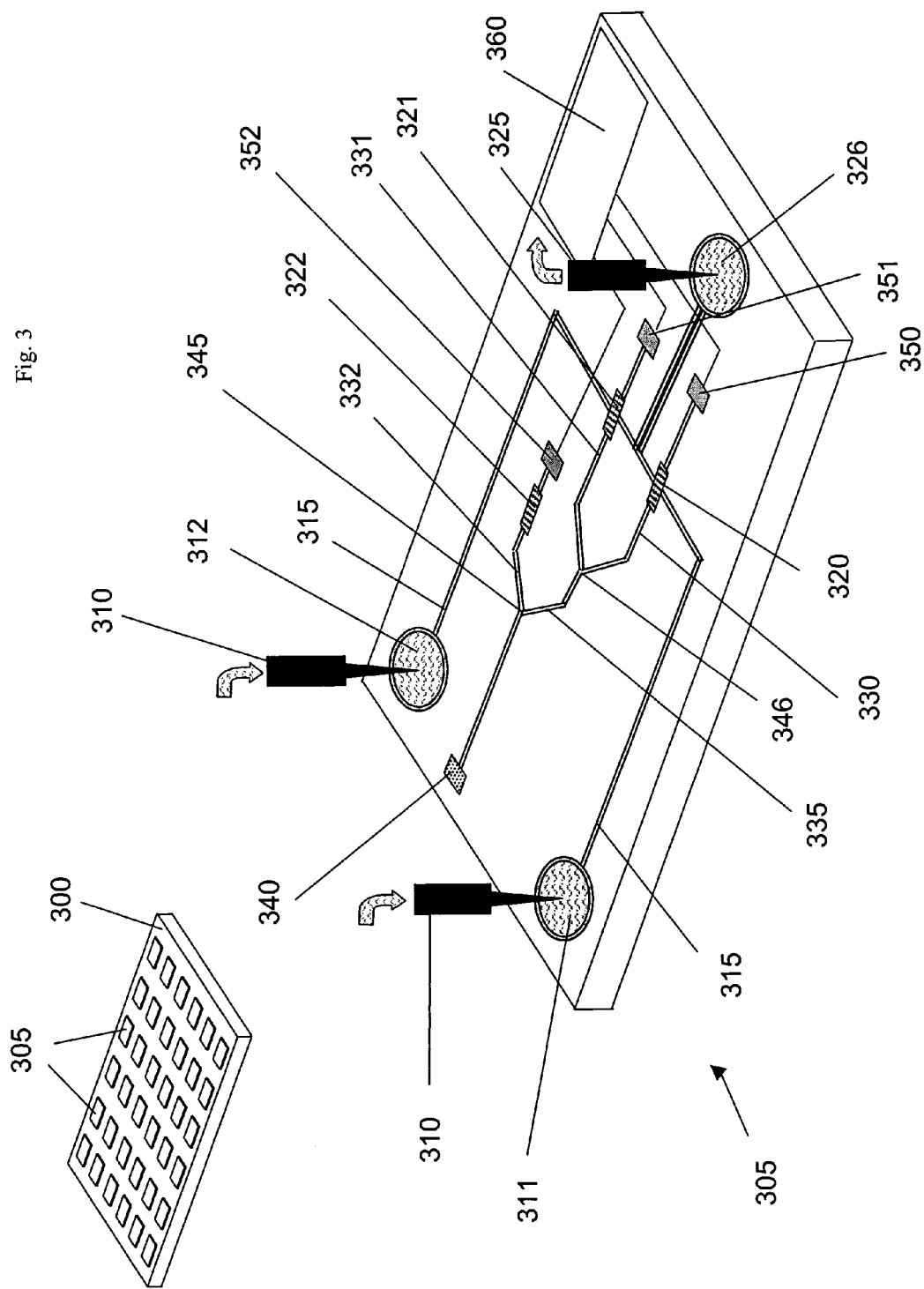
FIG. 3 shows a detection/identification subsystem of a detection system according to an embodiment of the present invention.

Referring to FIG. 3, a multi-channel DMA 300 includes at least one to hundreds of individual detector modules or chips (hereafter "modules") 305, each designed to respond in a highly specific manner to one particular target agent. If one module 305 detects the presence of the particular target agent, then the specific module 305 reporting the decision automatically determines the identification of that target agent. A specific conjugate molecule or detector molecule (e.g., antigen or antibody) (hereafter "detector molecule") bound to a grating, that in turn binds the target agent within the working fluid, determines agent specificity. With the exception of specific detector molecules per detector module, all other features of each module 305 are identical.

The detector module 305 identifies agents in the working fluid 50. Micro-pipette dispensers 310 at a sample arm inlet reservoir 311 and control arm inlet reservoir 312 on the module 305 introduce the working fluid 50 containing potentially hazardous agents, as well as other inert material, to the module 305. Each reservoir 311, 312 typically holds 100-1000 nL of solution. Micro-fluidic channels 315 having exemplary cross sectional areas of approximately $10 \times 10\, \mu m^2$ to $100 \times 100\, \mu m^2$, direct the solution, i.e., working fluid and inert materials, in the sample and control arms to porous polymer Bragg gratings 320, 321. Pressure gradients, or alternatively, electrokinetics, may induce fluid flow within the micro-fluidic channels 315. In the case of electrokinetic inducement, additional electrodes in the module move the solution along the channel by electrophoresis and/or electroosmosis. The porous Bragg gratings 320, 321 allow the solution to flow through. An outlet micro-pipette 325 collects the material at the outlet reservoir 326. Proper filtering in the collection subsystem 20 and dispenser subsystem 60 of FIG. 1 ensures that particles are small enough to pass through the pores of the gratings 320, 321. However, sample grating 320 acts chemically as a "selectively sticky" filter through detector molecules that are bound in the pores and/or on the surface of the sample grating 320. Inert materials flow through the filters of subsystems 20 and 60 and the sample grating 320, but target agents are selectively bound to a corresponding detector molecule and become a permanent part of the grating. Optically, the porous polymer Bragg gratings 320, 321, 322 act as narrow band spectral filters with a reflection or transmission notch that is highly sensitive to refractive index changes. The selective binding modifies the refractive index of the grating. The control grating 321 has no detector molecules and hence does not selectively trap any target agents. All material that is not trapped is swept through the filters to the outlet reservoir 326 and then through the outlet micro-pipette 325. When a particular agent is present in the solution, the ID subsystem 70 is sensitive to the refractive index changes in the gratings 320, 321. If the refractive index changes, a transduction mechanism then provides a signal to alert the system 70 of the presence of an agent.

In addition to the Bragg gratings 320, 321, 322 described above, each module 305 consists of an optical channel waveguide 335 comprised of three arms: (1) a sample arm 330, (2) a control arm 331, and (3) a reference arm 332. All three arms contain identically fabricated porous polymer Bragg gratings 320, 321, 322. The porous polymer Bragg gratings 320, 321, 322 have been integrated onto the module along with a light source 340, waveguides 335, waveguide splitters 345, 346, micro-fluidic channels 315, photodetectors (i.e., photodiodes) 350, 351, 352 and processing electronics 360. The response from each arm 330, 331, 332 is continuously and simultaneously monitored and processed electronically to factor out environmental disturbances, including inert material in the sample, to achieve a high sensitivity and a low false alarm rate.

Light is launched into the waveguide from the light source 340, which may be a broadband light emitting diode ("LED") or preferably a single-frequency laser diode ("LD"). At the first Y-splitter 345, a portion of the light is directed to the reference arm 332 containing a reference grating, and subsequently, a photodetector 352. The reference grating is hermetically sealed; it never is exposed to the working fluid 50. The reference grating may or may not contain a pure solution in its pores. The optical properties (e.g., index of refraction) of the reference grating change only due to thermal changes in the system. The light detected by the photodetector 352 in this arm 332 changes only due to thermally induced changes in the reference grating, energy fluctuations, or drift of the light source. The remaining energy at the first Y-splitter 345 is directed to a second Y-splitter 346 where the energy is split into two equal parts and directed to the sample 330 and control 331 arms of the detector module 305.

The sample 330 and control 331 arms contain the activated sample grating 320 and the unactivated control grating 321, respectively. The location of the porous polymer Bragg gratings 320, 321, 322 may be in the channel waveguide or in the waveguide cladding that form the sample 330, control 331, and reference 332 arms. Each grating is constructed to reflect light at the same wavelength over a very narrow spectral band. Foreign material passing through the filters produces modifications to the refractive index. The modifications shift the spectral location of the reflection notch and produce a change in the transmitted light detected by the photodetectors 350, 351. Energy detected at the photodetectors 350, 351 will also change due to thermal drift of the reflection notch or light source fluctuations. The fluctuations are removed by taking the difference of the sample grating 320 and control grating 321 signals. Alternatively, the processing electronics 360 can subtract the reference grating arm 332 signal from both the sample grating 330 and control grating 331 arm signals. Since all three gratings 320, 321, 322 and their respective photodetectors 350, 351, 352 are located on the same module 305, the gratings 320, 321, 322 experience the same fluctuations due to thermal drift, light source fluctuations, and other disturbances. This process thus removes spurious signals due to the detector environment. The reference grating arm 332 can also maintain the wavelength of the light source tuned to the Bragg grating 322. As the Bragg grating notch drifts due to thermal drift, the signal from the reference grating arm 332 passes through a feedback loop to the light source 340 to tune the wavelength of the source to the notch wavelength of the Bragg grating 322. The remaining signals are the result of foreign material, i.e., agents, present in the working fluid. Inert material passes through the gratings and produces transient changes in the refractive index. As a result, transient signal responses are produced at the photodetectors 350, 351. The signals from the sample grating 330 and control grating 331 arms are integrated over an appropriate time interval (e.g., by sample and hold circuits) and then subtracted (e.g., by a differential amplifier). Since both arms, 330 and 331, identify, on the average, the same amount of inert material, these signals will cancel, producing a null signal. However, if target agents, i.e., molecules, are present, the target agents stick to the sample grating 320 and permanently change its refractive index. Moreover, the refractive index change increases with each captured target agent. Since the reflection notch is spectrally narrow, a relatively small change in refractive index produces a large change in filter transmittance. The subsequent change in the transmitted light over the integration interval upsets the balance in the two arms 330 and 331. The difference signal is passed through a differential amplifier in the electronic processor 360. The presence of a non-zero signal heralds the presence of the target agent. Once a target agent detection is accomplished, that specific detector module 305 is replaced before the system is used in another monitoring scenario.

Figure 4:
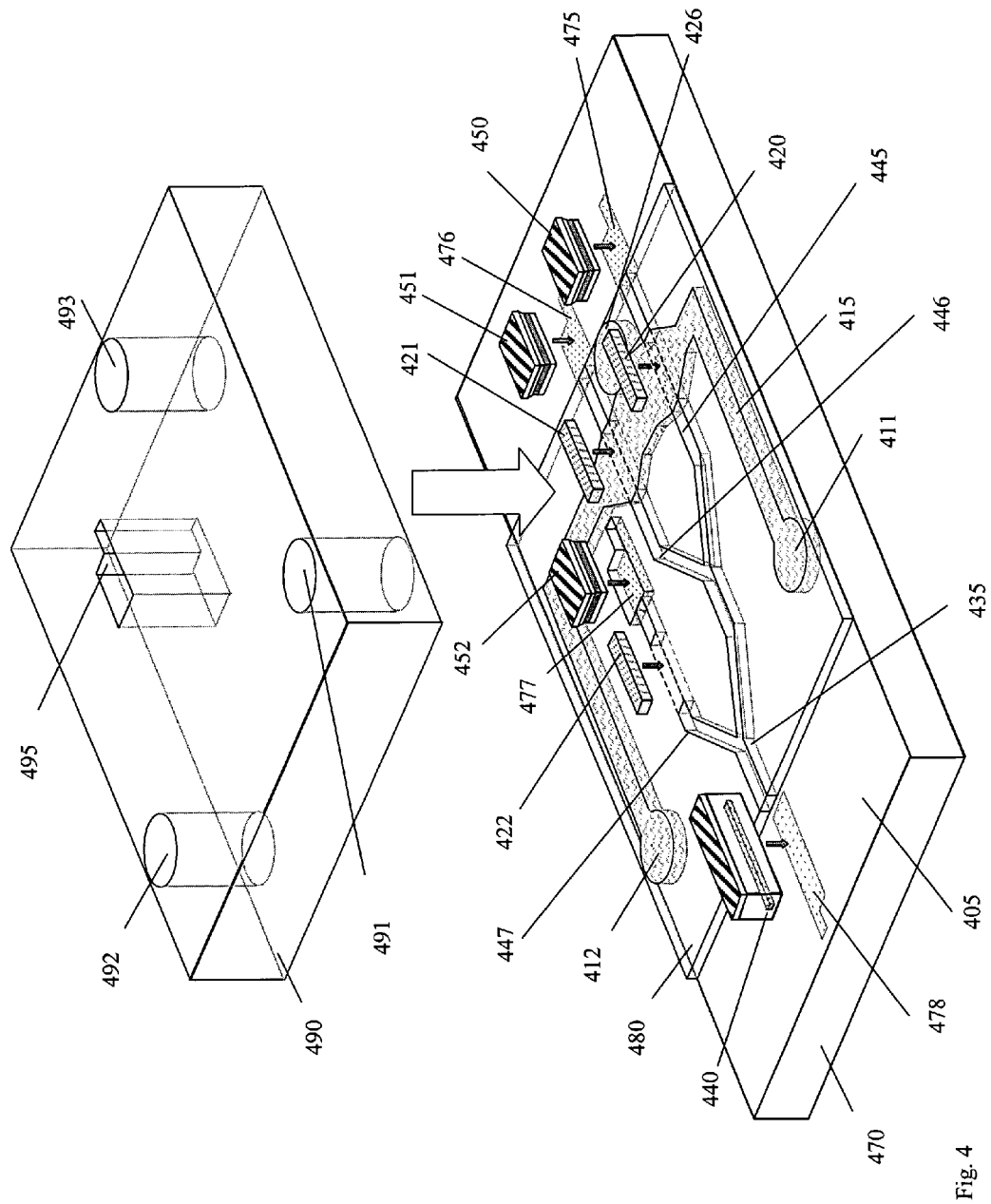
FIG. 4 shows a waveguide circuit according to an embodiment of the present invention.
Figure 5:
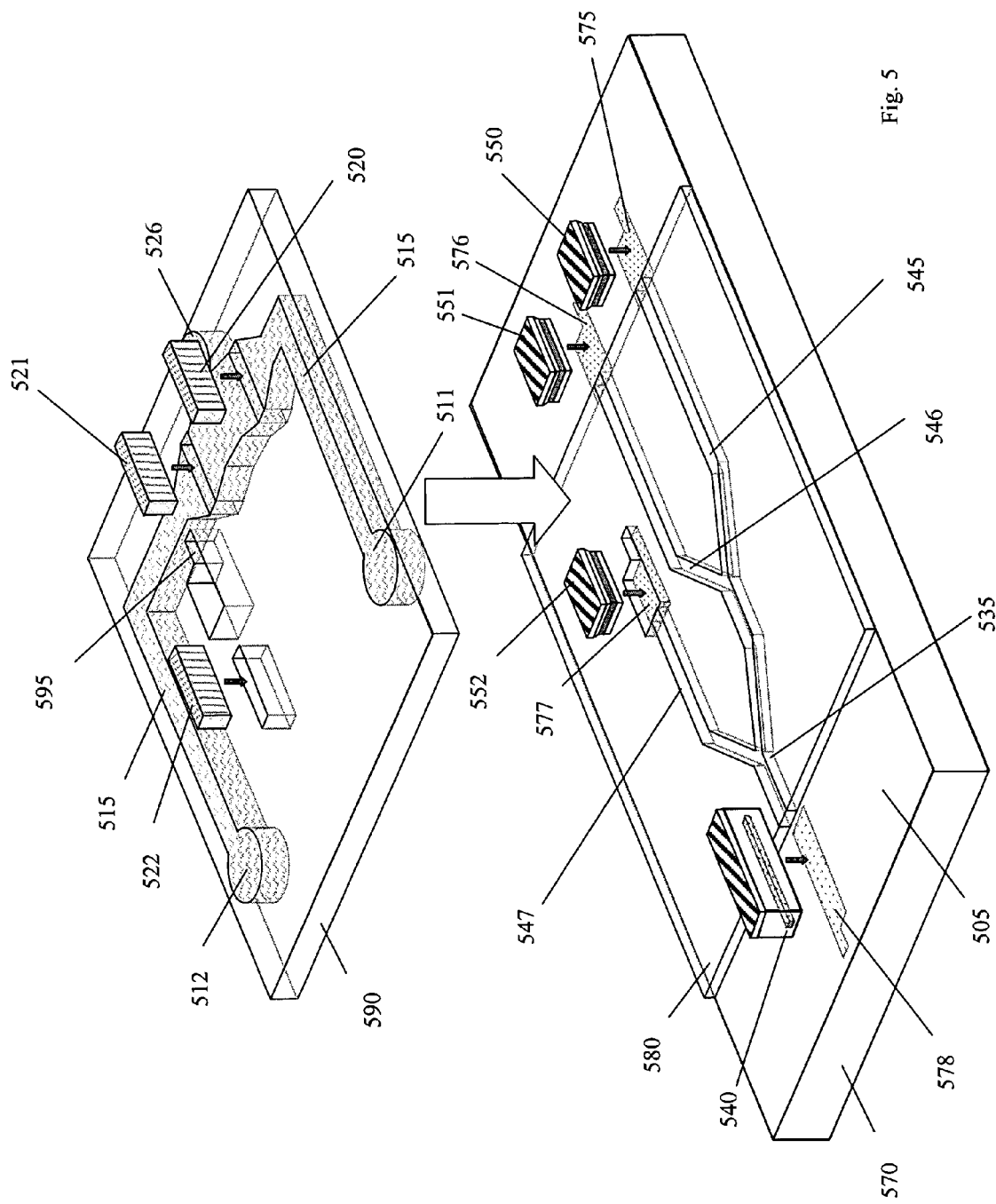
FIG. 5 shows a waveguide circuit according to an embodiment of the present invention.

In addition to the component parts of the detection module 305 shown in FIG. 3, FIGS. 4 and 5 provide additional description of component parts according to an embodiment of the present invention. Referring to FIG. 4, detection module 405 includes a light source 440, a channel waveguide 435, gratings 420, 421, 422, a micro-fluidic circuit 415, photodetectors 450, 451, 452, and processing electronics. The processing electronics are not shown in FIGS. 4 and 5. The module 405 resides on a silicon wafer 470. Light source 440, photodetectors 450, 451, 452, and large scale integration processing circuitry are either mounted directly on the silicon wafer 470 or integrated monolithically with the silicon wafer 470, at electrodes 475, 476, 477, 478. The silicon wafer 470 is coated with a silicon dioxide ($SiO_2$) layer 480. A silicon oxynitride (SiON) channel waveguide 435 along with sample 445, reference 446, and control 447 arms, resides in this layer. Micro-fluidic circuit 415, as well as the fluid input 411, 412 and output 426 ports, are etched in the $SiO_2$ layer 480. The $SiO_2$/SiON channel waveguide 435 and micro-fluidic circuit 415 are covered with a glass slab 490.

The Bragg gratings 420, 421, 422 are situated in the channel waveguide 435. To form the Bragg gratings 420, 421, and 422, a rectangular cavity is etched in the channel waveguide 435 at the position selected for each of the gratings. This cavity is then filled with a pre-polymer syrup described herein, and a porous polymer grating is formed by the procedures discussed further with respect to at least FIGS. 14a-14c. Micro-fluidic circuit 415 is etched in the $SiO_2$ layer 480 as shown, and the micro-fluidic channels are directed in a substantially perpendicular direction to the long dimension side of the gratings 420, 421. In this manner, the working fluid of the device will flow through the porous gratings 420, 421 at an angle substantially perpendicular to the channel waveguide 435 axis. In one embodiment, the surface of layer 480 is exposed to air. However, in an alternate embodiment, the $SiO_2$/SiON waveguide circuit 435 and micro-fluidic circuit 415 are covered with a glass sheet 490 to seal the micro-fluidic circuit 415 and the porous polymer Bragg gratings 420, 421, 422 from the environment, e.g., air. Small pilot holes 491, 492, 493 are etched in the glass 490 to match up with the inlet/outlet ports 411, 412, 426 of the micro-fluidic circuit 415 on the module 405. An electrical feed-through 495 is also provided for reference photodetector 452.

Referring to an alternative embodiment in FIG. 5, detection module 505 resides on a silicon wafer 570. A $SiO_2$ layer 580 is coated with a polymer layer 590, such that the polymer has an index of refraction smaller than the SiON channel waveguide 535. Porous polymer Bragg gratings 520, 521, 522 are situated in the polymer cladding layer 590. Micro-fluidic circuit 515 is etched in the polymer cladding layer 590. The fluid input 511, 512 and output 526 ports are likewise etched in the polymer layers 590. The polymer cladding 590 includes an electrical feed-through 595 for the reference photodetector 552. A laser diode 540 and photodetectors 550, 551 contact electrodes 575, 576, 577.

Alternatively, the Bragg gratings 520, 521, 522 are situated in the cladding directly above the channel waveguide 535. The $SiO_2$ layer 580 containing the SiON channel waveguide 535 is coated with a polymer cladding 590. A rectangular cavity is etched in the polymer cladding 590 at the positions selected for the gratings. This cavity is then filled with a pre-polymer syrup described herein, and a porous polymer grating is formed by the procedures discussed further with respect to at least FIGS. 14a-14c. Micro-fluidic circuit 515 and inlet/outlet ports 511, 512, 526 are etched in the polymer cladding 590 as shown, and the micro-fluidic channels are directed in a substantially perpendicular direction to the long dimension side of the gratings 520, 521. In this manner, the working fluid of the device will flow through the porous gratings 520, 521 at an angle substantially perpendicular to the channel waveguide 545 axis. The polymer cladding 590 is exposed. Optionally, the polymer cladding 590 is covered with a glass sheet to seal the micro-fluidic channels 515 and the porous polymer Bragg gratings 520, 521, 522 from the outside environment. Small pilot holes are etched in the glass to match up with the inlet/outlet ports 511, 512, 526 of the micro-fluidic circuit in the polymer cladding 590.

With respect to FIGS. 4 and 5, the light sources 440 and 540 are preferably a laser diode ("LD"). In particular, tertiary semiconductor lasers, such as $Al_xGa_{1-x}As$, and quaternary semiconductor lasers, such as $In_{1-x}Ga_xAs_{1-y}P_y$, are useful, where the ratios x and y can be varied to adjust the laser wavelength. AlGaAs lasers generally provide wavelengths between 750 nm and 870 nm. $In_{1-x}Ga_xAs_{1-y}P_y$ lasers generally provide wavelengths between 1.1 μm and 1.6 μm. Visible wavelength lasers, such as GaInP (670 nm) and AlInP (584 nm), may also be useful. The LD is bonded upside-down to an electrode on the silicon surface and butt-coupled to the SiON channel waveguide.

Further, waveguides 435, 445, 446, 447, 535, 545, 546, and 547 may be formed of SiON as a core material. Depending on the nitrogen-to-oxygen ratio, the refractive index of SiON can be varied between 1.46 and 2.3. Thus, the SiON refractive index can be tuned to be greater than that of $SiO_2$ to form a waveguide. And, the refractive index can be matched to that of the polymer (approximately 1.52) used in the inline Bragg gratings, or tuned to be slightly larger than the polymer that is used as the cladding layer. Thus, it is possible to tune the index so that the porous polymer Bragg gratings can be situated directly in the channel waveguide, or in the waveguide cladding directly above the channel waveguide as described herein.

In further reference to FIGS. 4 and 5, the optical outputs of the reference 447, 547, sample 445, 545, and control 446, 546 waveguide channels are coupled to photodetectors 450, 451, 452, 550, 551, 552. The photodetectors 450, 451, 452, 550, 551, 552 are mounted upside-down and bonded to electrode pads 475, 476, 477, 575, 576, 577 on the silicon wafer 470, 570. For visible wavelengths from approximately 400 nm up to approximately 900 nm in the near infrared, silicon photodiodes may be used. For wavelengths in the range of about 900 nm to 1600 nm, AlGaAsP photodiodes may be used.

Referring to FIGS. 6a and 6b, an embodiment illustrates the type of electronic processing applied to the photodetector outputs for the sample and control channels of FIGS. 3, 4, and 5. Referring to an embodiment in FIG. 6a, only inert material flows through both the sample and control porous polymer Bragg gratings. Referring to an embodiment in FIG. 6b, target agents, along with the inert material, pass through the gratings. In each of FIGS. 6a and 6b, the electronic processing system consists of four main parts: (1) sample and hold circuits 600, 601; (2) differential amplifier 610; (3) analog-to-digital (A/D) converter 605; and (4) additional digital processing electronics 615.

The sample and hold circuits 600, 601 sample voltages from the photodetectors over a specified time interval. The time interval is selected by a negative pulse of a predetermined time interval applied to the gate of a p-channel MOSFET 670, which closes a switch and allows data in the form of a stream of voltage pulses from photodiodes to pass through the switch and be stored on a capacitor 620, 625. These pulses, as illustrated in the embodiment in FIG. 6a, represent transient responses from the photodiodes due to inert material flowing through the gratings and producing fluctuations in the average refractive index. This leads to the transmission of transient light pulses through the grating that are detected by the photodiodes. The sample and hold circuits receive input from a control data stream 630, 631 and corresponding gate pulse 635, 636, as well as sample data stream 640, 641 and corresponding gate pulse 645, 646. The input is received through amplifiers 675. The output of the sample and hold circuits 600, 601, at the end of the gate pulse, are dc voltages, $V_C$ 650, 651, for the control channel, and $V_S$ 655, 656, for the sample channel. $V_C$ and $V_S$ represent the sum of voltage spikes from their respective channel. These voltages are input to a differential dc amplifier 610 that employs one operational amplifier 660. The conventional offset-voltage balancing circuitry standard for differential amplifiers is not shown. The high gain of the operational amplifier 660 results in an output that amplifies the difference between the two input voltages by a factor approximately equal to the ratio of $R_2$ 662 to $R_1$ 661 (e.g., if $R_1$=1 kΩ and $R_2$=100 kΨ, $R_2/R_1$=100). On average, the same amount of inert material is expected to flow through both control and sample gratings. Output $V_{out}$ 665, 666, is equal to $(R_2/R_1)(V_S-V_C)$. Therefore, output $V_{out}$ 665 of the differential amplifier 610 should be approximately zero. The longer the sampling interval (i.e., the longer the gate pulse), the closer this output approximates zero when only inert material flows through the porous gratings. Output $V_{out}$ 666 does not equal zero. A standard A/D circuit 605 digitizes the output voltage. This data is stored and/or processed further. For example, averages are computed over several sampling intervals to improve the sample statistics. Other more complex data processing can also be accomplished. In the embodiment shown in FIG. 6b, target agents stick to the sample Bragg grating in sample data stream 641 resulting in a non-zero persistent voltage baseline on which transients, due to inert material, ride as voltage fluctuations. The output of the differential amplifier is non-zero, thus signaling a target-molecule detection event.

The above scheme also discriminates real signals from photodiode voltage fluctuations and drift that may occur due to light source power fluctuations, thermal drift, and other environmental disturbances. Since the two detector arms reside on the same module, they are subject to the same external disturbances. Voltages produced due to these effects are common to both channels and subtracted out by the differential amplifier.

Voltage drift due to external influences may also be factored out by using the output of the reference arm of the module in a set of circuits similar to those of FIGS. 6a and 6b, comparing the reference output with the sample and control outputs separately. Thermal drift may cause the Bragg grating notch to wander off the laser wavelength due to thermal changes in the refractive index. To optimize operation of the Bragg gratings, the reference arm photodiode may be used in a feedback loop to tune the laser wavelength to match any thermal drift of the Bragg gratings and lock the laser wavelength to the Bragg condition. Diode lasers are available whose output wavelengths can be tuned electronically over a few nanometers.

Figure 7:
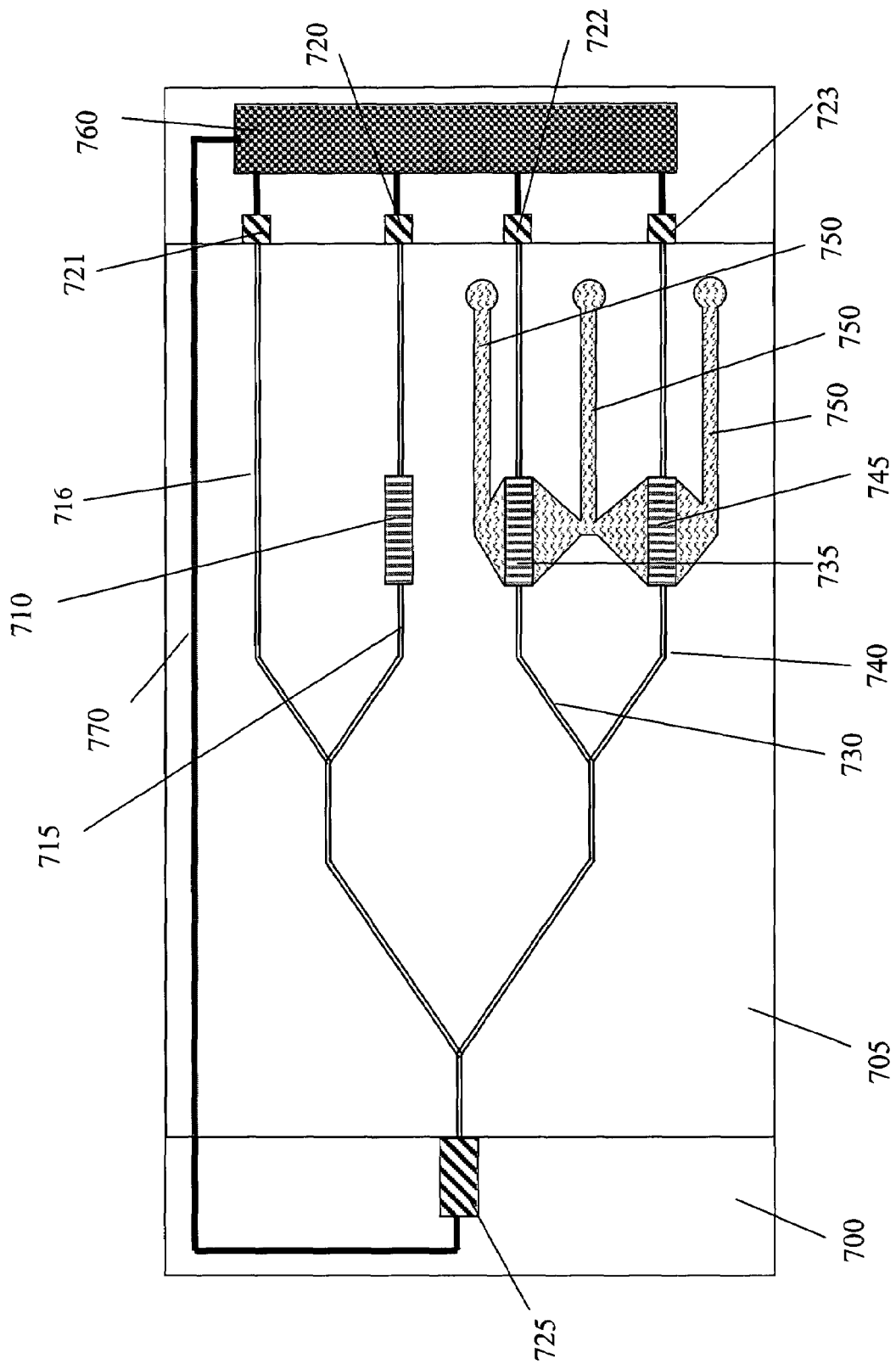
FIG. 7 shows an embodiment with dual reference arms according to the present invention.

To discriminate fluctuations and drift of the Bragg grating from those of the light source, in an alternative embodiment, the reference arm could be replaced with a dual reference arm using an additional Y-splitter. For example, referring to FIG. 7, a sealed porous polymer Bragg grating 710, on an $SiO_2$ layer 705 substantially coating a Si substrate 700, terminating at a photodiode 720, and the second reference arm 716 would have no grating and terminate at a separate photodiode 721. The outputs of the two reference arms 715, 716 are compared to discern thermal drift of the Bragg grating 710 from fluctuations or drift of the output power from the laser diode 725. Sample and control arms 730, 740 are directed to gratings 735, 745 proximate micro-fluidic channels 750. All photodiodes 720, 721, 722, 723 lead to an electronic processor 760 with an LD stabilization feedback loop 770 to the laser diode 725.

Referring to FIG. 25, in an embodiment of the present invention, a porous polymer Bragg grating 2500 is situated in a channel waveguide 2510. Light is confined to the waveguide 2510 by total internal reflection at the substrate 2550 and cladding 2540. Light at the Bragg wavelength propagating along the waveguide 2510 is reflected from the grating 2500 and propagates back along the waveguide 2510 in the opposite direction. Therefore, transmitted light at the Bragg wavelength is attenuated.

Figure 9:
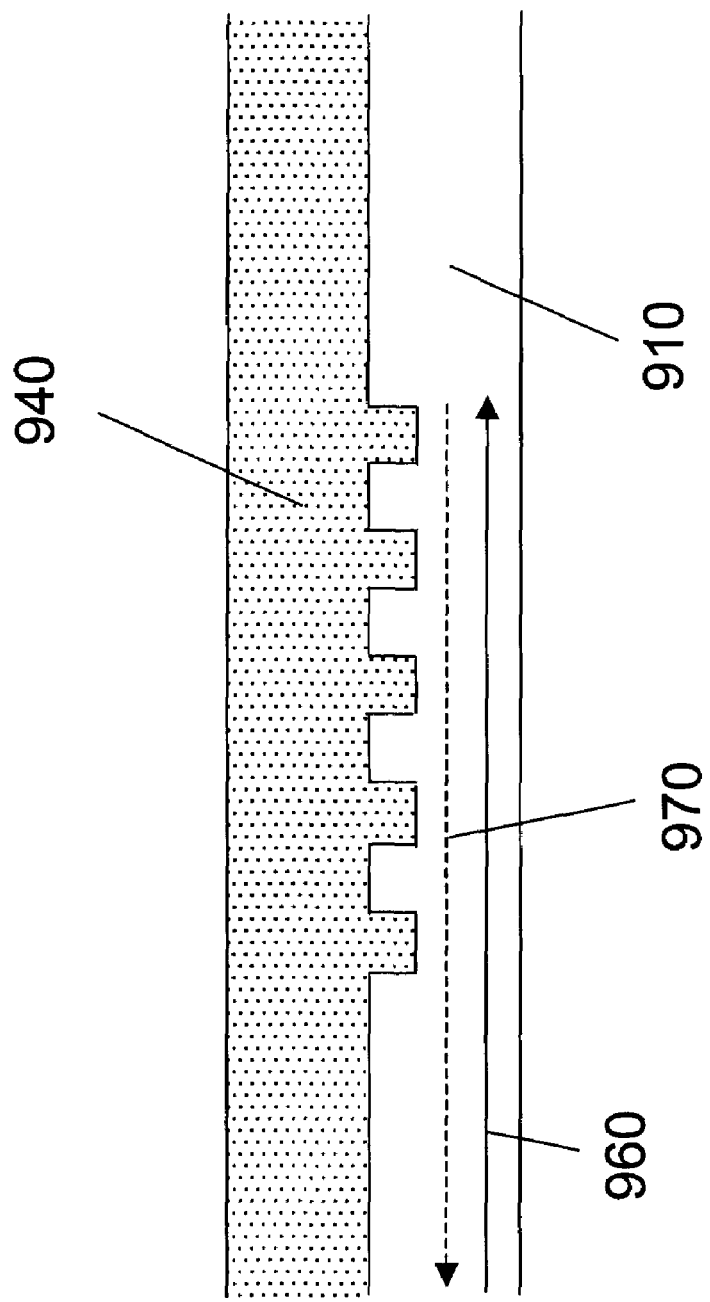
FIG. 9 shows a corrugated waveguide with a porous polymer cladding according to an embodiment of the present invention.

In an alternative embodiment of the present invention, referring to FIG. 9, a porous polymer medium serves as cladding 940 for a corrugated waveguide 910. In order to form cladding 940, the pre-polymer syrup is cured using a single incoherent beam of light such that no grating is recorded. The phase-separated liquid crystal is then removed to yield the porous polymer cladding. The corrugated waveguide 910 acts like a Bragg grating. Incident light is shown as 960 and reflected light is shown as 970 within FIG. 9. Light evanescently coupled to the porous cladding 940 will sense any change in the refractive index of the cladding 940. This would produce a spectral shift of the reflection notch of the filter. Changes in the refractive index of the grating change the efficiency of the evanescently coupled light.

Figure 10:
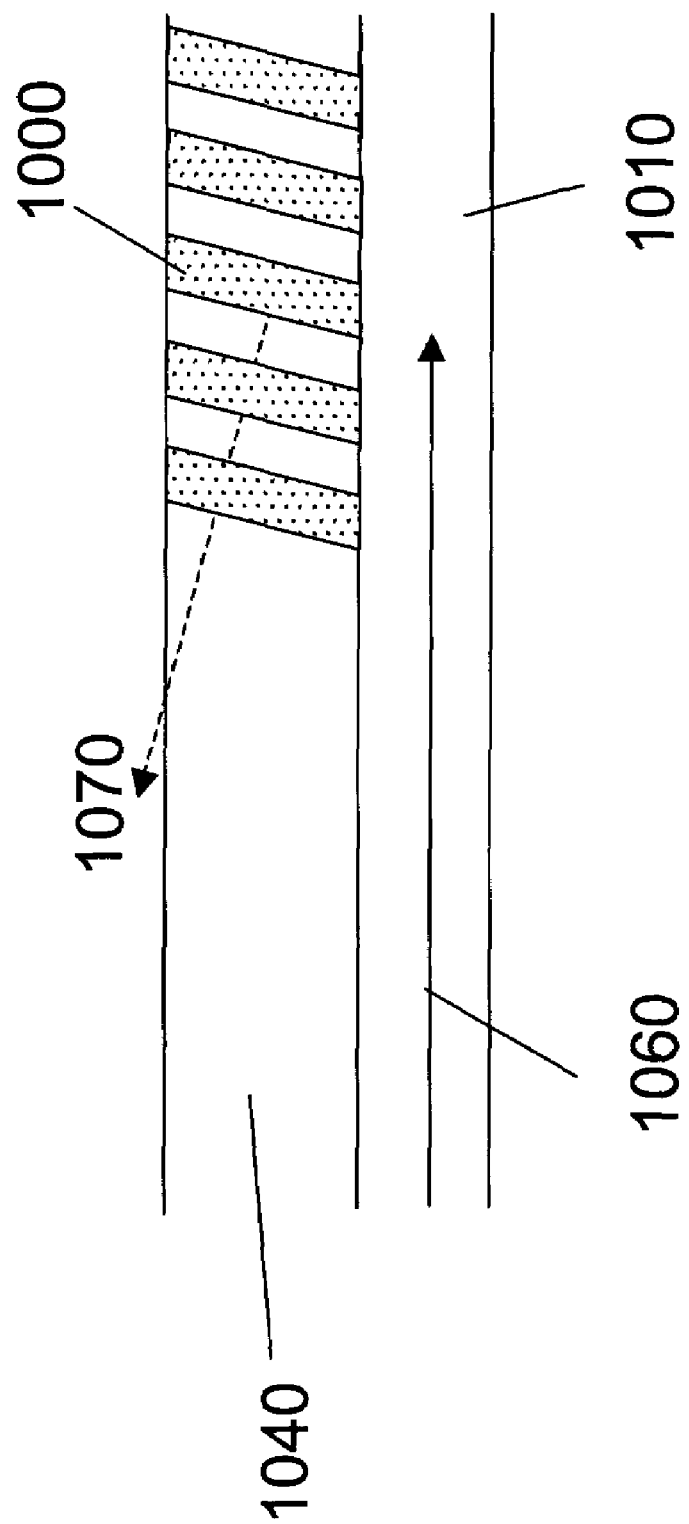
FIG. 10 shows a grating in cladding according to an embodiment of the present invention.
Figure 11:
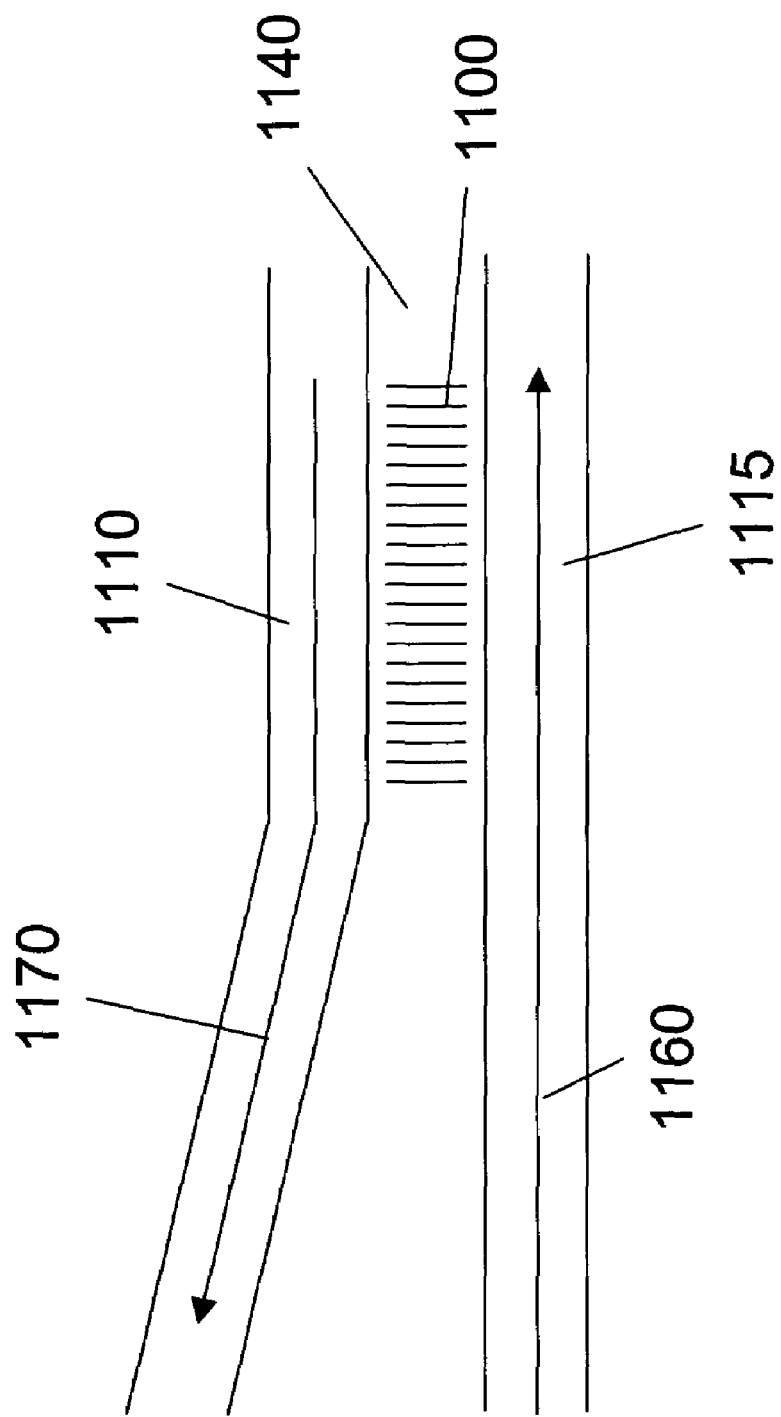
FIG. 11 shows channel waveguides according to an embodiment of the present invention.
Figure 12:
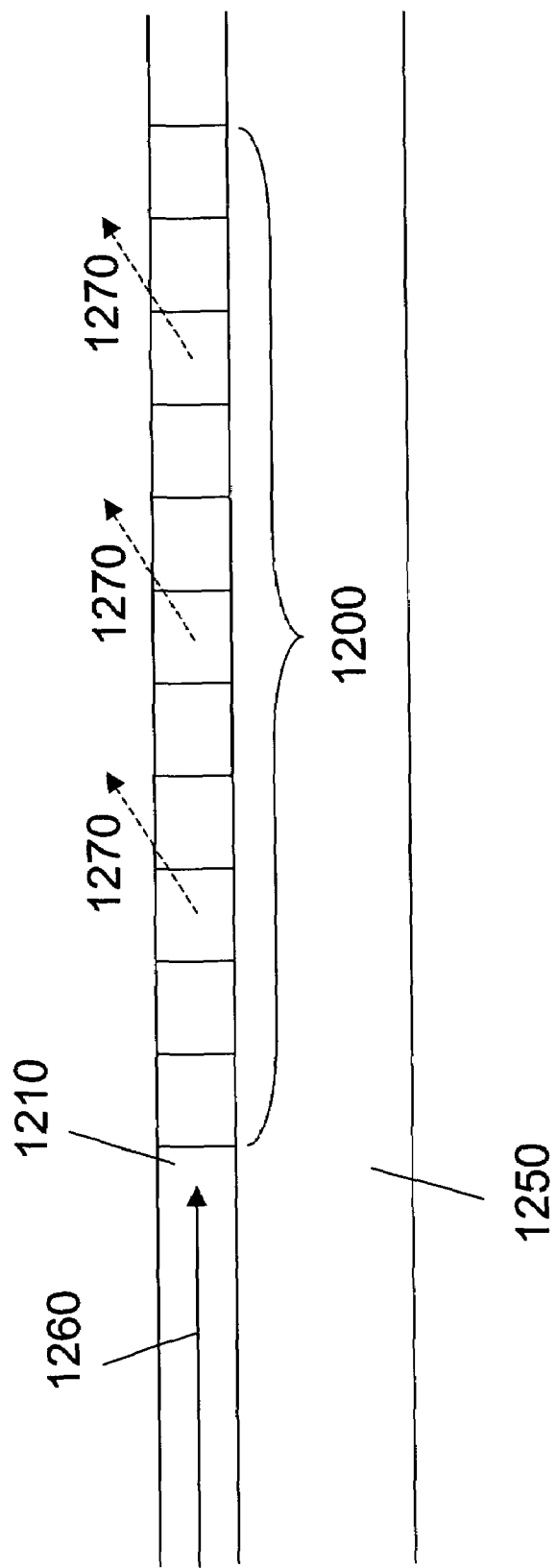
FIG. 12 shows a grating in a waveguide according to an embodiment of the present invention.
Figure 13:
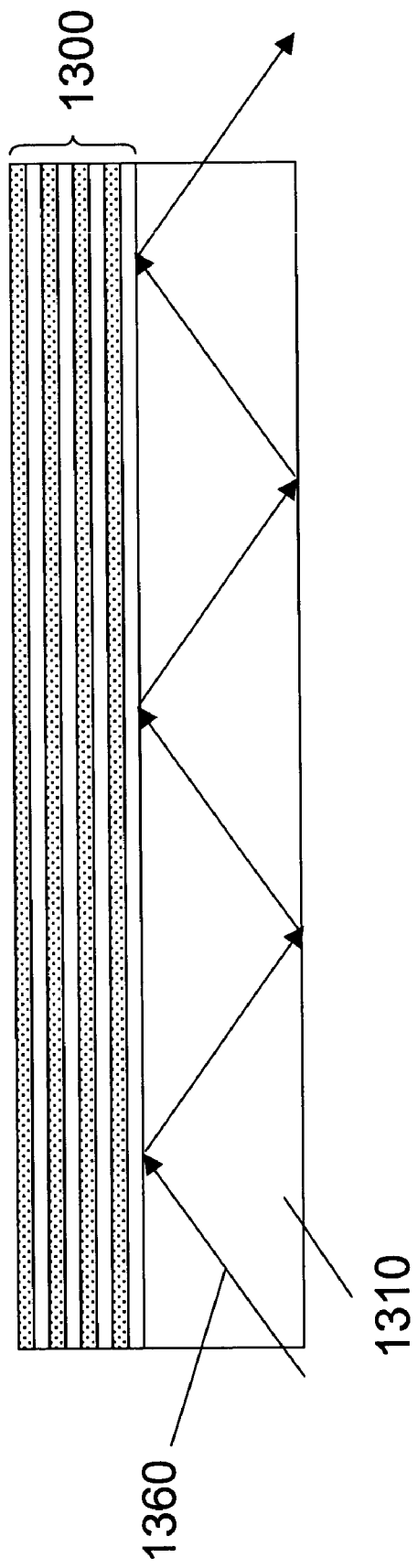
FIG. 13 shows a waveguide according to an embodiment of the present invention.

Changes in the refractive index of the grating affect the efficiency of the coupling at a specific wavelength. Referring to FIG. 10, an alternative embodiment places a porous polymer Bragg grating 1000 in the cladding 1040. Guided light 1060 through waveguide 1010 experiences spectrally selective loss to radiation modes 1070 by evanescently coupling to the Bragg grating 1000 in the cladding 1040. Referring to FIG. 11, two channel waveguides 1110, 1115 are coupled evanescently to form a waveguide coupler, directing outcoupled light 1170 and input light 1160. A holographic grating 1100 in the cladding region 1140 serves to spectrally assist this coupling for light at the Bragg wavelength. Outcoupled light 1170 is directed into the opposite direction in the output waveguide 1110. This configuration prevents reflected light from impinging back on the light source. Referring to FIG. 12, a long period, i.e., where Λ is substantially greater than λ, porous polymer grating 1200 is placed in a waveguide 1210 substantially on a substrate 1250. Such a grating 1200 serves to resonantly couple light 1260 at a specific wavelength to radiation modes 1270. Referring to FIG. 13, an asymmetric waveguide 1310 has a Bragg reflection grating 1300 serving as the substrate. Light 1360 resonantly coupled to the Bragg condition of the grating 1300 follows a zigzag path down the slab waveguide 1310.

In an alternative embodiment, a single Bragg grating in a waveguide channel can be used as a stand-alone detector element. Referring to top and side views, FIG. 8a and FIG. 8b, a porous polymer Bragg grating 800 is situated in a channel waveguide 810, as a stand-alone element, optically coupled to input optical fibers 820 and output optical fibers 830. Waveguide 810 and grating 800 are proximate to substrate 850. An LED or LD source 860 launches a wave into the fiber 820, which is coupled into the Bragg grating 800 and subsequently out-coupled to a miniature spectrometer (not shown), such as the S2000 manufactured by Ocean Optics Inc. The spectrometer monitors any real-time changes to the diffraction efficiency of the grating 800.

As referenced previously herein, certain embodiments of the present invention utilize polymer-dispersed liquid crystal ("PDLC") or holographic PDLC ("HPDLC") related technology in the formation of the Bragg gratings and waveguide components. Descriptions of PDLC materials and related technology can be found in U.S. Pat. No. 5,942,157, U.S. patent application Ser. No. 09/363,169 filed on Jul. 29, 1999 for Electrically Switchable Polymer Dispersed Liquid Crystal Materials Including Switchable Optical Couplers and Reconfigurable Optical Interconnects, U.S. patent application Ser. No. 10/235,622 filed on Sep. 6, 2002 for Electrically Switchable Polymer Dispersed Liquid Crystal Materials Including Switchable Optical Couplers and Reconfigurable Optical Interconnects, U.S. application Ser. No. 10/303,927 filed on Nov. 26, 2002 for Tailoring Material Composition for Optimization of Application-Specific Switchable Holograms, and U.S.patent application Ser. No. 60/432,643 filed on Dec. 12, 2002 for Switchable Holographic Polymer Dispersed Liquid Crystal Reflection Gratings Based on Thiolene Photopolymerization, each of which is incorporated by reference herein in its entirety. In a preferred embodiment of the present invention, the Bragg gratings comprise static holograms formed through holographic polymerization of a PDLC material using coherent light beams. As is described above with reference to FIGS. 14a-14c, after holographic polymerization, the liquid crystal is removed from the film. Extraction of the liquid crystal leaves pores within the remaining polymer matrix approximately 100 nm in diameter. The pores within the polymer matrix contain binding sites, such as COOH or $NH_2$, for a detector molecule. In a particular example, the polymer may be thiol-ene, thiol-acrylate, or one of various multifunction acrylates described in U.S. Pat. No. 5,942,157. Depending on the polymer composition, the polymer can be cured via visible or ultraviolet ("UV") laser radiation. The evacuated polymer matrix is then chemically treated to activate the binding site for the detection molecule. The activation procedure depends on the functional group of the binding site. For example, if the functional group is COOH, then amine coupling, e.g., EDC (N-ethyl-N'-(3-dimethyl aminopropyl)-carbodiimide hydrochloride) and NHS (N-hydroxysuccinimide), is an accepted procedure commonly referred to as EDC/NHS coupling procedure. Alternatively, for the activation of $NH_2$, an accepted procedure is cross-linking to free amino groups via polymerized gluteraldehyde. Any method that activates the binding site to bind to a detector molecule is sufficient. Next, a detector molecule is bound to the activated binding site. This detector molecule then can sense a target agent of interest. The detector molecule can be an enzyme, a protein, an antibody, or an antigen. The detector molecule is specifically selected to bind to the target agent. After activation and detector molecule attachment, the binding sites that are unattached to any detector molecule are blocked using conventional means. The blocking is usually achieved with a large protein, such as casein or BSA. When the target agent binds to the detector molecule, it causes a change in the refractive index of the polymer, thus causing a shift in the wavelength of the holographic notch.

Figure 14:
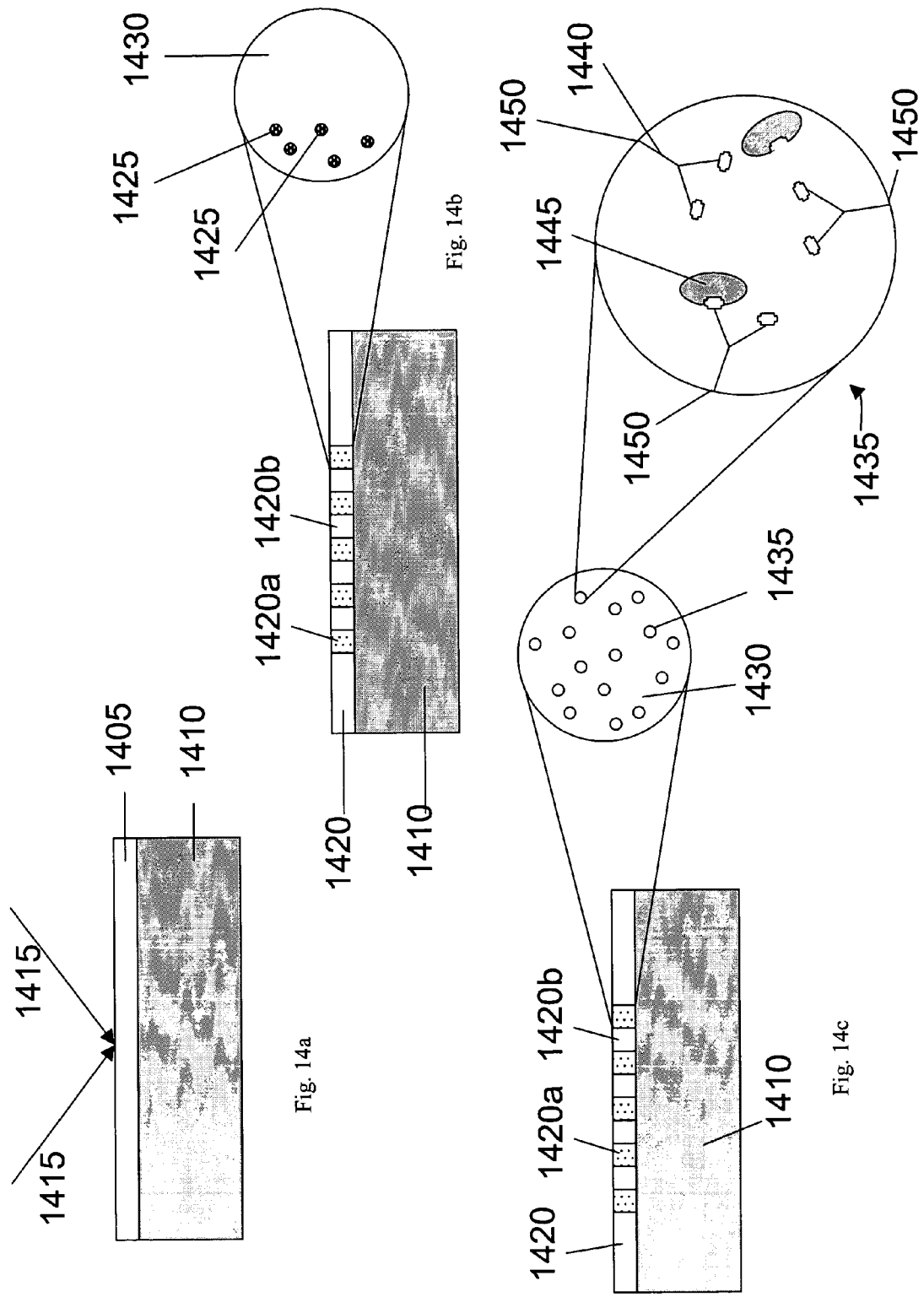
FIGS. 14a-14c show a fabrication process for gratings according to an embodiment of the present invention.

In a further embodiment of the present invention, described herein is the structure and formation of the Bragg gratings. Referring to FIG. 14a, a pre-polymer syrup consisting of a mixture 1405 of polymerizable monomer, photoinitiator, co-initiator, liquid crystal, binding site monomer, and in alternative embodiments, a cross-linking monomer and a long chain aliphatic acid are spread in a thin layer, typically about 10 μm, in slab waveguide format on a substrate 1410. In this embodiment of the present invention, two coherent beams of light 1415 are incident on the mixture 1405, forming a pattern consisting of PDLC 1420a and polymer 1420b channels within the mixture 1405, as shown in FIGS. 14b and 14c. In this embodiment, the polymerized material 1420 is referred to as HPDLC material, since the overlapping coherent beams 1415 form an interference pattern within the photopolymerized material 1420. During photopolymerization, portions of monomer from mixture 1405 are consumed forcing the remaining monomer to diffuse and replace the consumed portions of monomer, forming polymer channels 1420b. This diffusion displaces liquid crystal in mixture 1405 since it does not participate in the photochemical reaction, and the liquid crystal diffuses to channels 1420a. As the local liquid crystal concentration increases over time, the miscibility gap for the liquid crystal/polymer solution is eventually breached, and the liquid crystal separates out as a distinct phase in channels 1420a. A more detailed description of this process is found in U.S. Pat. No. 5,942,157.

Referring to FIG. 14b, the liquid crystal phase takes the form of interconnected nanoscale droplets of liquid crystal 1425 within a polymer matrix 1430. The nanoscale domains of liquid crystal 1425 are of controllable density and size. The liquid crystal 1425 is then extracted by: (1) soaking the hologram with a solvent followed by drying; (2) vacuum evacuating the pores; or (3) a combination of (1) and (2).

Referring to FIG. 14c, as a result of the liquid crystal extraction from the polymer matrix 1430, there remains an open structure of interconnected voids or pores 1435 (hereafter "pores"), where the pores 1435 are periodically distributed in the photopolymerized material 1420. The resulting hologram with pores 1435 is then treated chemically to activate the binding sites 1450 then attach detector molecules 1440 (i.e., antibodies) to the activated binding sites 1450. As described further herein, antigens 1445 may attach to detector molecules 1440. The Bragg grating formed by this process may then be used in the detector modules described with reference to, for example, FIGS. 5-7, in order to detect target agents within the working fluid. The polymer matrix 1430 has a refractive index of about 1.52, while that of the aqueous solution is approximately 1.33. The periodic index mismatch creates an index modulation or an optical grating. The grating exhibits Bragg diffraction for light at a specific wavelength propagating at a specific angle of incidence. For light propagating in the plane of the film, the hologram is a Bragg reflection grating that retro-reflects light at the Bragg wavelength. The Bragg wavelength is determined by the average refractive index and the periodic spacing of the porous regions. The strength of the reflection, i.e., the diffraction efficiency, is determined by the magnitude of the index modulation and the physical length of the filter, i.e., region of index modulation. Generally, the diffraction efficiency will become larger with increased filter thickness, and the spectral width of the reflection notch will decrease with increased filter thickness. The index modulation is determined by the difference in refractive indices of polymer matrix and aqueous solution, which in this exemplary embodiment is approximately 0.19, and the density of pores. A low index modulation can thus be achieved by a low density of pores. In a preferred embodiment, a small density of pores, i.e., low index modulation, and a thick filter is achieved in a waveguide configuration, resulting in a spectrally narrow filter with large diffraction efficiency. Nonetheless, the specific pore density must be consistent with a sufficient flow rate of working fluid through the hologram. Specific grating compositions are described further below.

The selected Bragg wavelength is determined by such factors as the chosen laser wavelength and the spectral region of sensitivity desired for detecting a refractive index shift based on the polymer and detector molecule reaction selected. This optical region may be anywhere across the visible or near infrared spectrum. The grating period $\Lambda$ is selected by forming a hologram with a recording wavelength $\lambda_r$ and an angle of incidence $\Lambda_r$ of the incident beams, with $\Lambda=\lambda_r/2 \sin \theta_r$. Thus, either $\lambda_r$ or $\theta_r$, or both, can be varied to form the desired grating period. The Bragg wavelength $\lambda_B$ for light propagating substantially along the waveguide axis is approximately $2n\Lambda$, where n is the average refractive index of the medium at $\lambda_B$. The index n changes as target agents are bound to the polymer matrix. The Bragg wavelength $\lambda_B$ is given by:

$$\lambda_B = 2n(\lambda_r/2 \sin \theta_r)$$

The bandwidth $\delta\lambda$ of the spectral diffraction efficiency for a Bragg grating is given by:

$$\delta\lambda = \frac{\lambda_B^2}{\pi n}\sqrt{\kappa^2 + (\pi/L)^2}$$

where $\kappa$ is the coupling constant of the grating and L is the grating thickness. The coupling constant is further given by $\kappa=\pi n_1/\lambda_B$, where $n_1$ is the amplitude of the index modulation of the grating. For sufficiently thin gratings, the bandwidth is inversely proportional to the thickness. Thus, a thicker grating leads to a sharper reflection notch. The thicker grating also increases the diffraction efficiency. For sufficiently thick gratings, the bandwidth is directly proportional to $\kappa$. Thus, a small coupling constant $\kappa$ (i.e., a small index modulation) also leads to a narrow spectral notch. Generally, a thick filter with a small index modulation yields a grating with high peak diffraction efficiency and a narrow spectral notch.

The index modulation of the grating is produced by the periodic variation of nanoscopic pores throughout the volume of the polymer. Typically, the density of pores has the form of a rectangular wave, with a volume fraction of pores $f_c$ in a channel of width $\alpha\Lambda$, ($0<\alpha<1$) and no pores in adjacent channels of width $(1-\alpha)\Lambda$. The index modulation is related to the first Fourier component of the Fourier expansion of this rectangular wave, and is given by:

$$n_1 = \frac{2f_c}{\pi}\sin(\alpha\pi)(n_p - n_s)$$

where $n_p$ and $n_s$ are the refractive indices of the polymer and solution filling the pores, respectively. The parameters $f_c$ and $\alpha$ are determined by the phase separation of liquid crystal during the recording of the holographic grating. These are controlled by processing parameters such as recording intensity and total exposure, as well as material properties including liquid crystal concentration and concentrations of other recipe constituents, such as long chain aliphatic acids. With the refractive indices relatively fixed at $n_p$ approximately equal to 1.52 and $n_s$ approximately equal to 1.33, the index modulation is directly controlled by the values of $f_c$ and $\alpha$.

Figure 15:
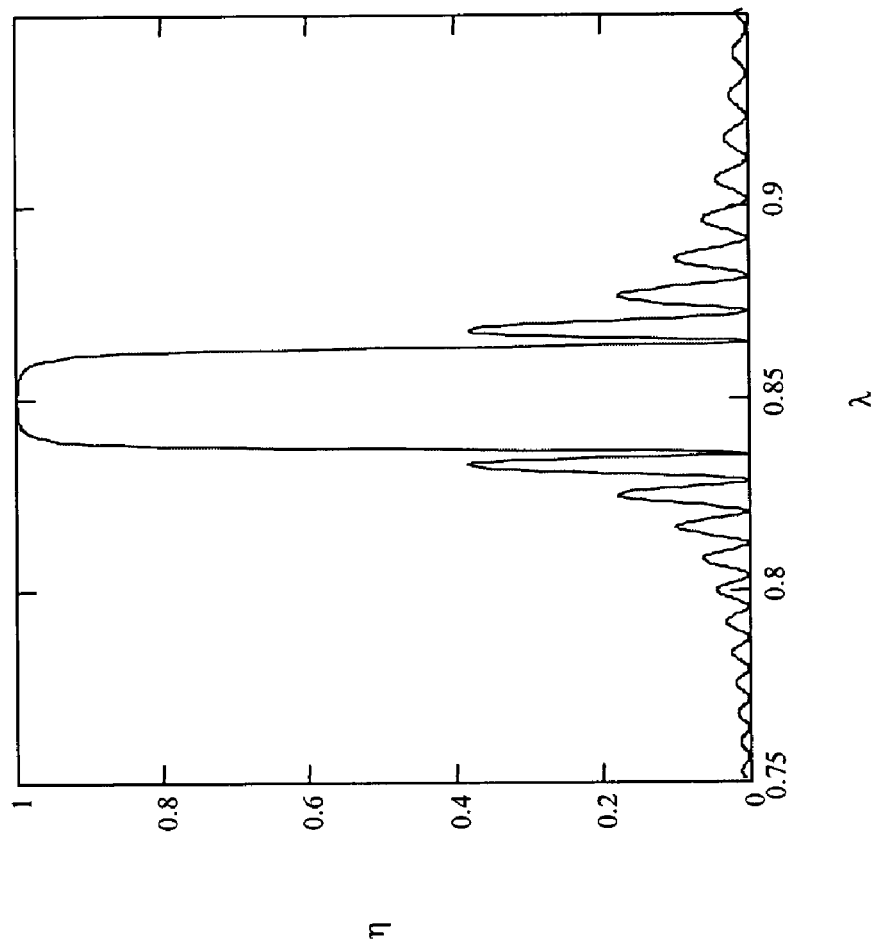
FIG. 15 shows a spectral diffraction efficiency according to an embodiment of the present invention.

Referring to FIG. 15, in an exemplary embodiment of the present invention, the spectral diffraction efficiency of a grating with $f_c=0.4$, $\alpha=0.3$, and $L=25$ μm is shown. The index modulation $n_1$ is 0.039. Alternatively, referring to FIG. 16, a filter response with the same peak efficiency has a reduced bandwidth. For this grating, $f_c=0.1$, $\alpha=0.3$, and $L=100$ μm. The corresponding index modulation $n_1$ is 0.0098. A filter at least this thick is readily achieved in a waveguide configuration. A sharper reflection notch gives a more sensitive change in transmittance with changes in refractive index. A holographic recording method for creating a porous polymer grating enables users to set processing parameters in order to easily obtain the index modulation for the sharp reflection notch.

Figure 16:
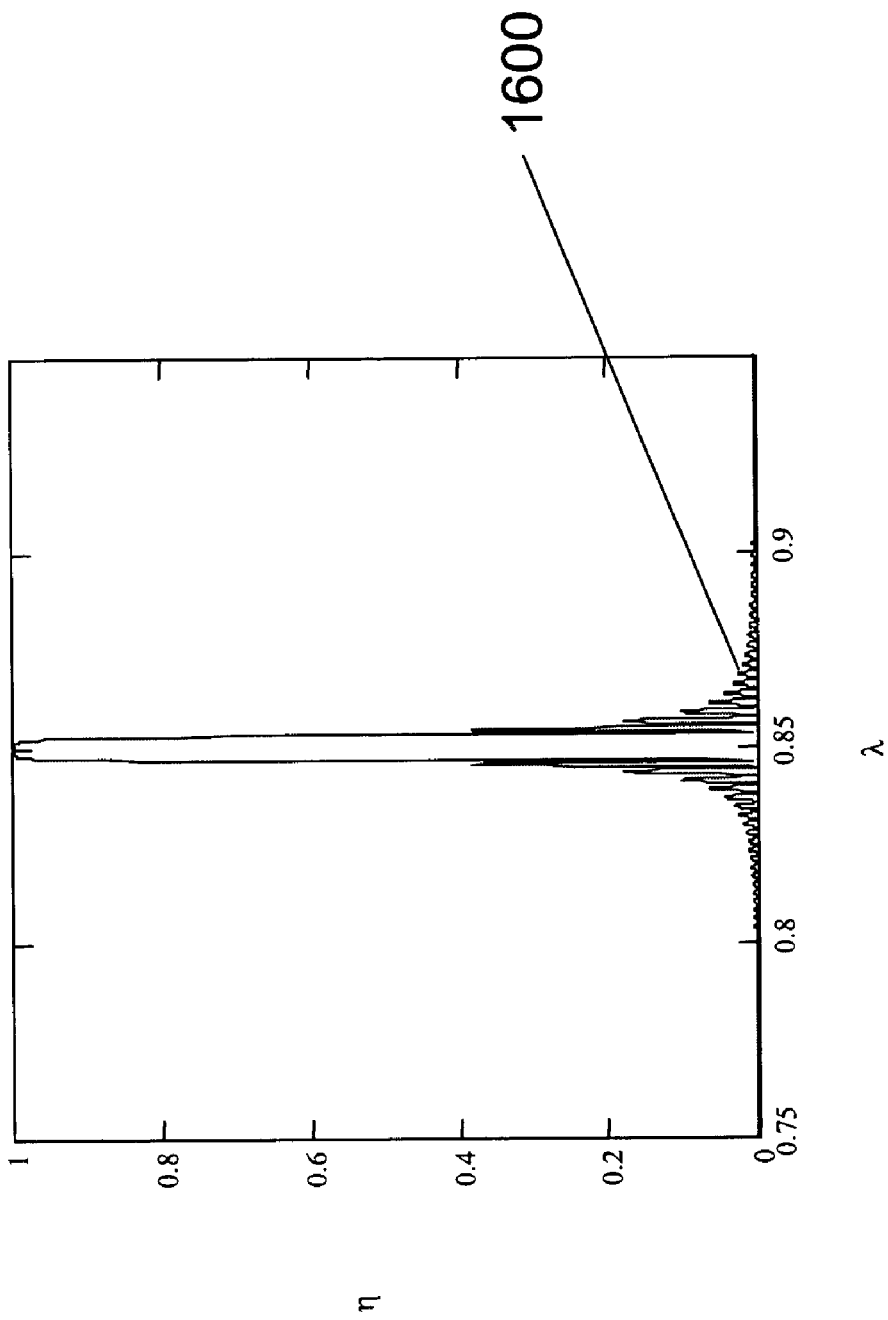
FIG. 16 shows a spectral diffraction efficiency according to an embodiment of the present invention.
Figure 17:
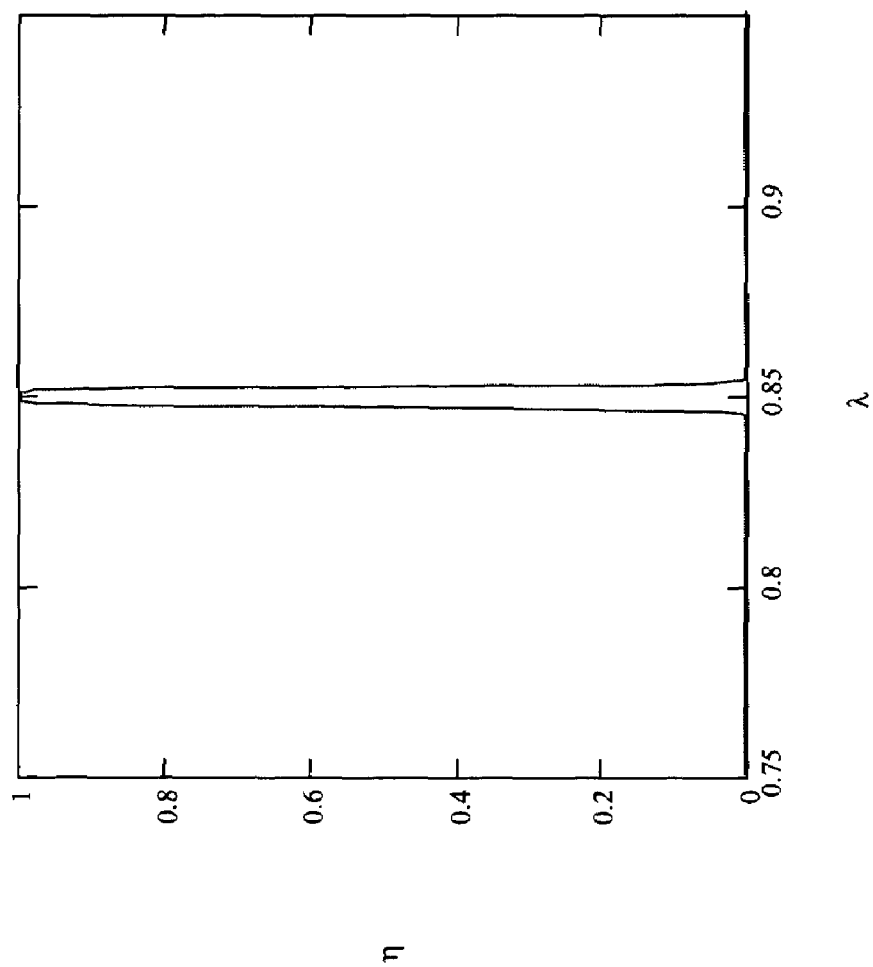
FIG. 17 shows a spectral diffraction efficiency according to an embodiment of the present invention.

The presence of sidelobes 1600, such as those shown in FIG. 16, in certain applications leads to ambiguous signals. Sidelobes 1600 are naturally occurring features of all volume gratings with uniform index modulation. Inducing a non-uniform index modulation in the grating eliminates sidelobes, a process called apodization. Apodization is readily achieved using holographic techniques. Referring to FIG. 17, the plot exemplifies the spectral efficiency of a grating with Gaussian apodization. This filter has the same peak efficiency as the embodiment in FIG. 16, but is sharper and has no sidelobes. For this grating, $L=280$ μm. The peak index modulation in the middle of the grating is $n_1=0.0098$. However, the index modulation amplitude falls off as a Gaussian function toward the front and back of the grating. Such a grating is obtained holographically by giving the recording beams a Gaussian intensity distribution.

Figure 18:
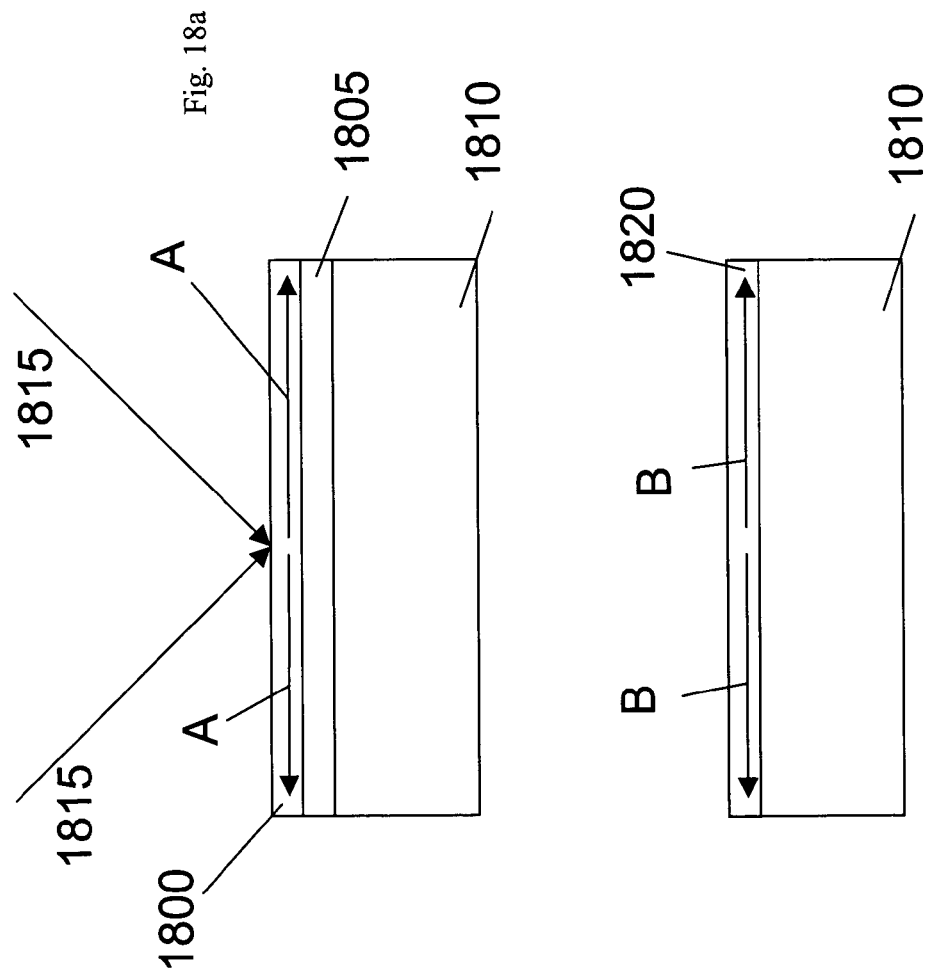
FIGS. 18a-18c show a process for obtaining an intensity distribution according to an embodiment of the present invention.

As exemplified in FIG. 18a, Gaussian intensity distribution is achieved by passing the beams 1815 through at least one neutral density filter 1800, over a pre-polymer syrup mixture 1805 on a substrate 1810, with optical density that has an inverse Gaussian distribution. Other filters or masks can produce other types of apodizing functions, such as raised cosine, hyperbolic tangent, polynomial, or other apodizations based on mathematical distributions. The transparency of the at least one neutral density filter 1800 substantially decreases in the direction of arrows A. Referring to FIGS. 18b and 18c, since the pore density that forms in the PDLC hologram 1820 is a function of the local intensity, resulting grating 1822 has a pore distribution that follows the local intensity of the recording beams 1815. The transparency of the PDLC hologram 1820 substantially increases in the direction of arrows B as shown in FIG. 18b. Referring to FIG. 18c, the resulting grating 1822 has alternate polymer slabs 1830 and porous slabs 1835. The pore density of the porous slabs 1835 substantially decreases in the direction of arrows C.

Sensitivity is built into the detection in two ways. First, there is an optical differential gain. The filter reflection or transmission notch is very sharp spectrally and exhibits a large change in transmittance for a relatively small change in refractive index. Second, there is an electronic differential gain. Signals from the sample and control arms are detected and processed in an electronic differential amplifier that produces a large output for a relatively small difference between the two signals. See FIGS. 6a and 6b for processing electronics.

To build specificity into the sample gratings, the binding sites of the pores or polymer matrix of the holograms are chemically activated and the detector molecules are bound to the polymer matrix. Thus, if a target agent is present in the working solution, it will selectively bind to the detector molecules. The target agent becomes trapped in the pore. Since the chemical nature of the polymer matrix changes, the average refractive index also changes. Consequently, the spectral properties of the porous polymer Bragg grating also change.

Bound target agents modify the spectral properties of the sample grating by changing the refractive index and possibly swelling the polymer. The diffraction efficiency of the sample grating is very sensitive to these changes. The spectral shift $\Delta\lambda_B$ of the grating is determined by $$\frac{\Delta\lambda_B}{\lambda_B} = \frac{\Delta n}{n} = \frac{\Delta\Lambda}{\Lambda}$$

Figure 19:
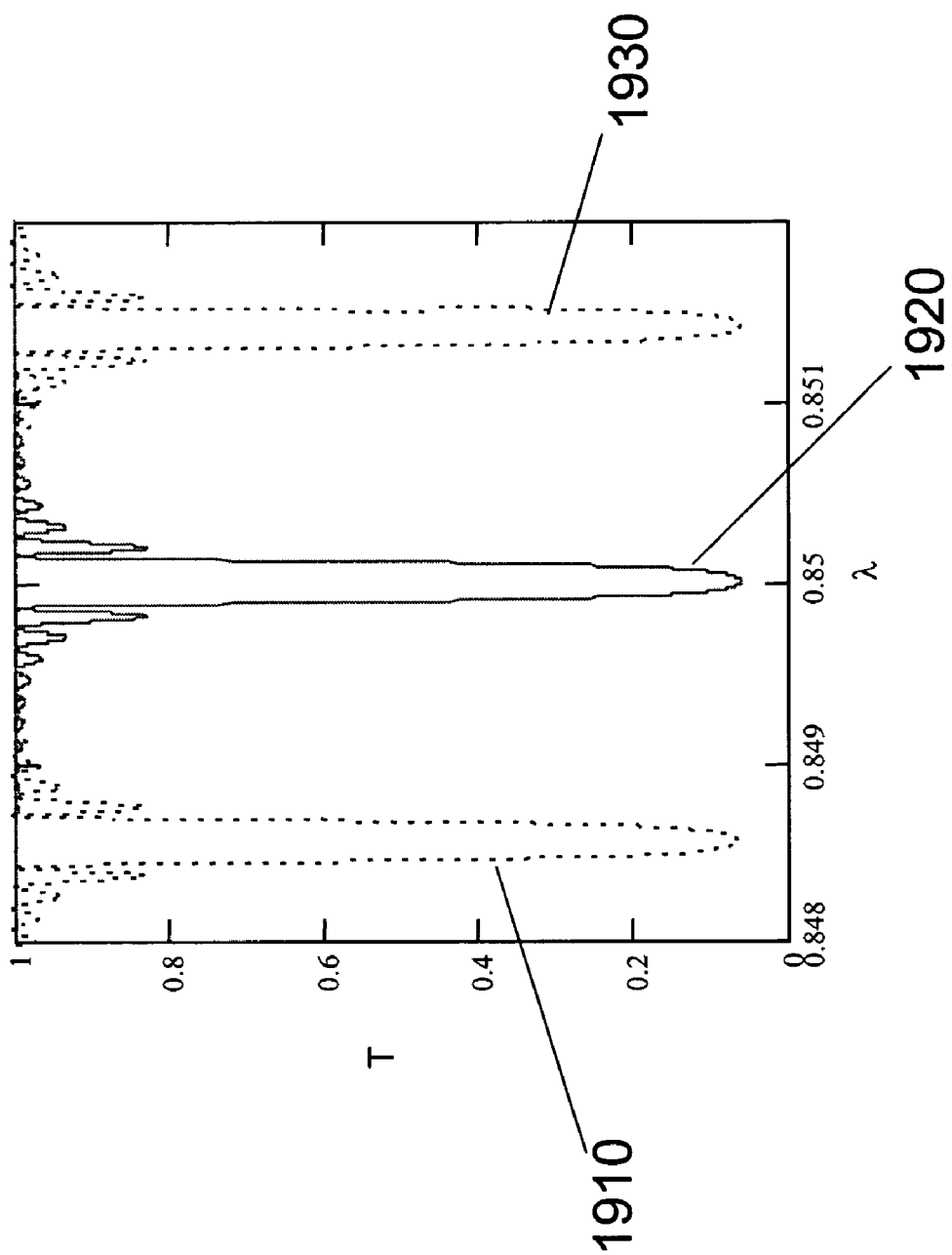
FIG. 19 shows transmission notches for different refractive indices according to an embodiment of the present invention.

For example, let the Bragg wavelength be $\lambda_B$=850 nm for a grating with an average index n=1.5 and grating period $\Lambda$=283 nm. Thus, a spectral shift of $\Delta\lambda_B$=1 nm is produced by $\Delta n/n = \Delta\Lambda/\Lambda = 0.0012$, i.e., $\Delta n$=0.00183, or $\Delta\Lambda$=0.33 nm. A spectral shift of 1 nm produces a very significant change in the transmittance of the filter. Referring to FIG. 19, three transmission notches are shown for three different refractive indices for a filter irradiated by a broadband light source, e.g., LED. The center notch 1920 for n=1.5000 is centered spectrally at $\lambda$=0.850 µm or 850 nm. Transmission notch 1910 shifts with a decrease of index, while transmission notch 1930 shifts with an increase in index. The effects are similar to the swelling of polymer, i.e., a change of grating period. An index change of $\Delta n$=±0.0025 shifts the notch by greater than 1 nm and changes the transmission substantially, from about 5% to about 100%, at 850 nm.

Figure 20:
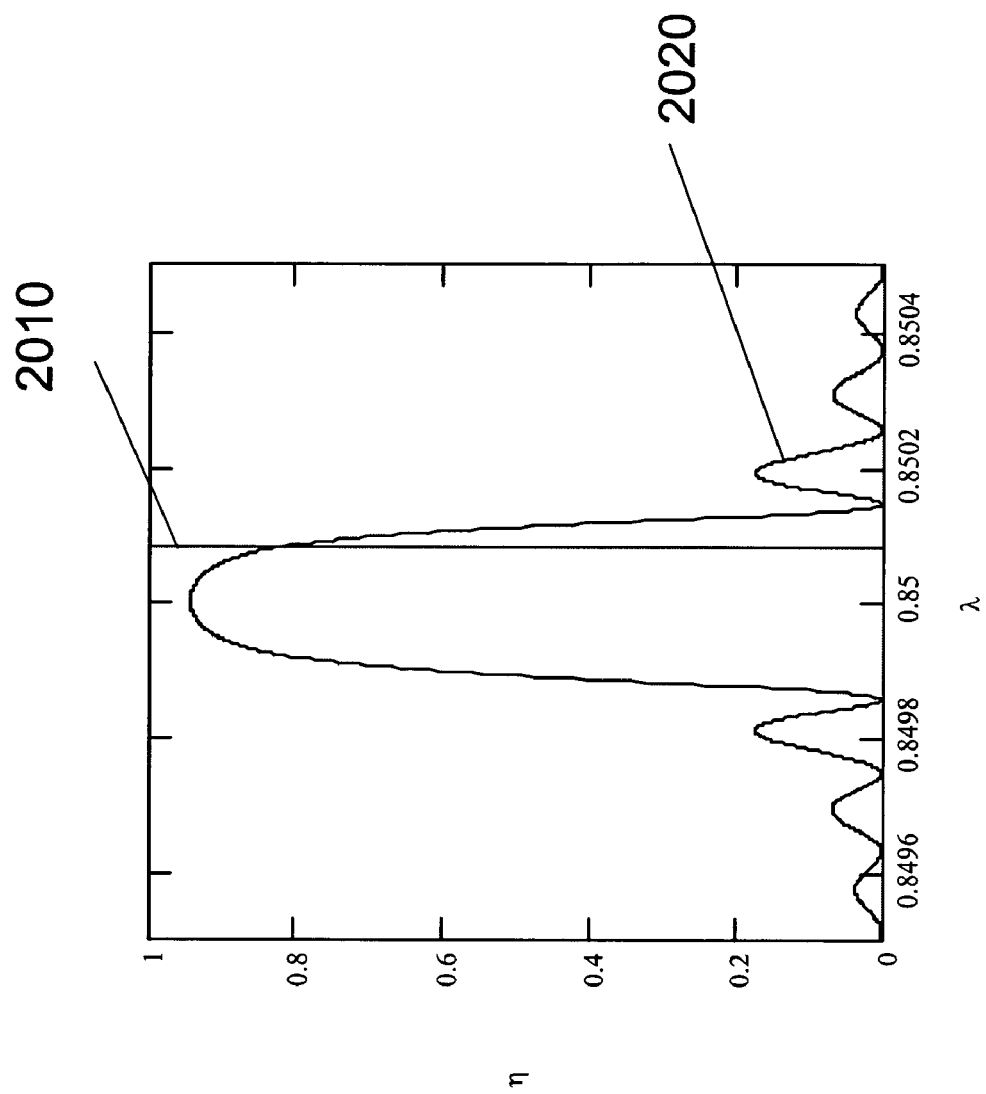
FIG. 20 shows a spectral diffraction efficiency according to an embodiment of the present invention.

The sensitivity of the sample grating may be enhanced by interrogating the grating at a wavelength near a region of rapidly changing efficiency. The diffraction efficiency $\eta$ (i.e., reflection; transmission equals $1-\eta$) for a Bragg grating is given by:

$$\eta = \tan h^2(\kappa L)$$

where $\kappa$ is the coupling coefficient and L is the filter thickness. The relative change $\Delta\eta/\eta$ in diffraction efficiency is given by:

$$\frac{\Delta\eta}{\eta} = 8.4 \frac{\eta}{\kappa L} \frac{L}{\lambda_L} \Delta n$$

and $$\frac{\Delta\eta}{\eta} = 16.8 n^2 \frac{\eta}{\kappa L} \frac{L}{\lambda_B^2} \Delta\Lambda$$

for changes in refractive index and grating period, respectively. Referring to FIG. 20, $\kappa L$=2.1, L=2 mm, $\lambda_B$=850 nm, and n=1.5. The laser wavelength $\lambda_L$ 2010 is approximately 850.075 nm. A readily detectable change in efficiency 2020 of $\Delta\eta/\eta$=0.05 is achieved with just $\Delta n$=6.5×10$^{-6}$ or $\Delta\Lambda$=1.2× 10$^{-3}$ nm. Referred to as optical differential gain, a relatively small change in index or period produces a relatively large change in transmittance.

Figure 21B:
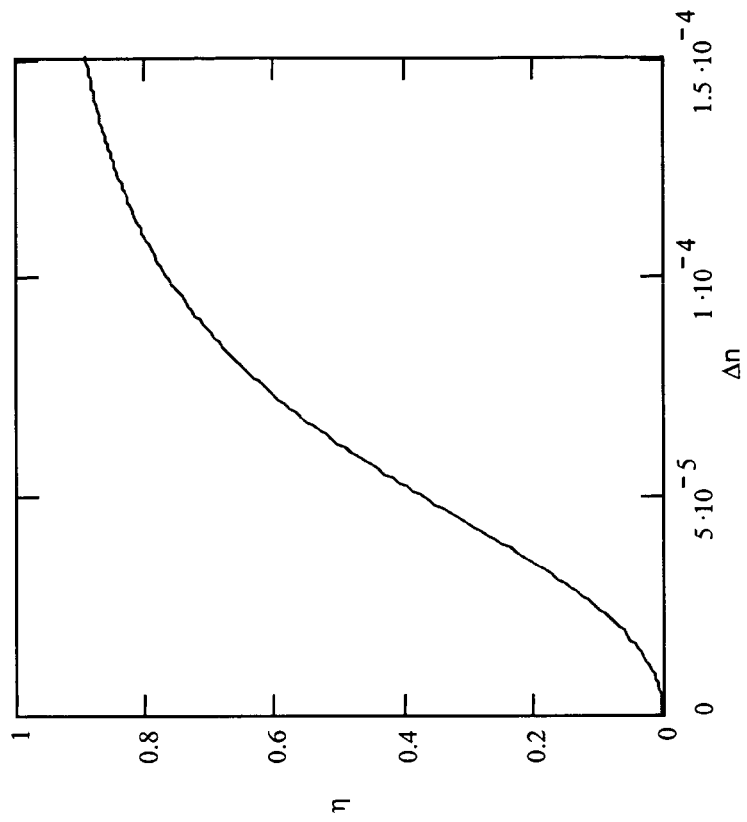
FIGS. 21a and 21b show a spectral diffraction efficiency according to an embodiment of the present invention.
Figure 21A:
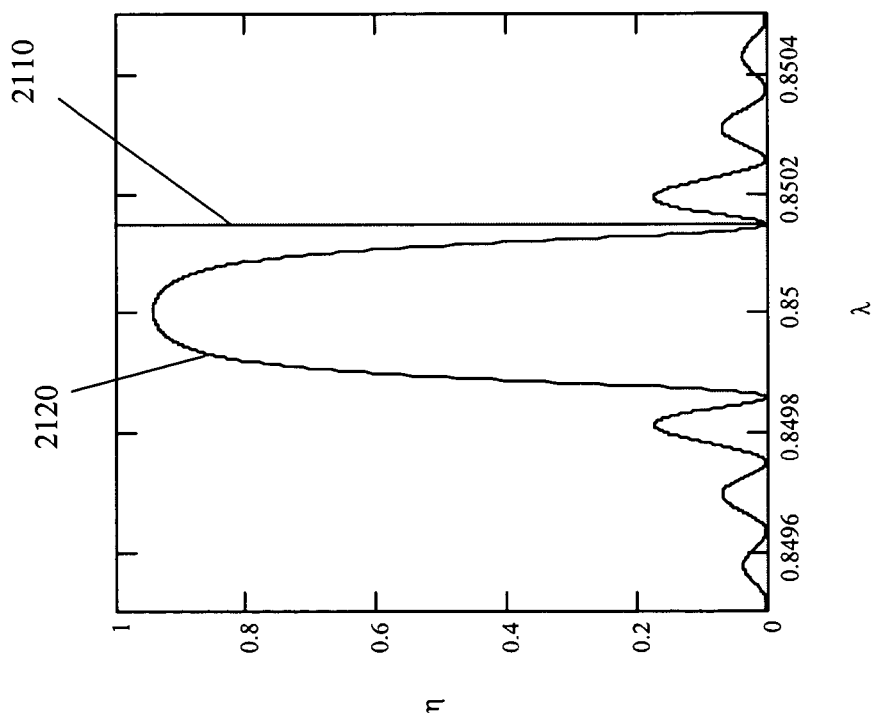

Referring to FIG. 21a, as another exemplary embodiment, the laser wavelength 2110 is at a null in the diffraction efficiency. A small change in refractive index then produces a rapid rise in the diffraction efficiency 2120 from a zero background. The benefit of this effect is realized when the photodetector is placed to view reflected light rather than transmitted light. Referring to FIG. 21b, the embodiment is exemplified as a plot of diffraction efficiency $\eta$ as a function of $\Delta n$ at $\lambda$=0.8501448 µm.

The following embodiments are set forth herein to describe exemplary materials and grating configurations that were useful as detectors in experiments conducted in free space. One skilled in the art recognizes the configuration changes necessary to incorporate such examples into the waveguide embodiments contemplated by the present invention.

In a first exemplary embodiment, gratings are constructed using thiol-acrylate as the polymerizable monomer and 2-carboxyethylacrylate (2-CEA) as the binding site monomer, with 10-µm thickness achieved by sandwiching the mixture between two glass plates. These gratings have one glass substrate coated with a release agent. The release agent substrate is removed, and the gratings are evacuated in a vacuum oven over a period of approximately three days to remove the liquid crystal. The cells are scanned in, for example, a Cary 500 UV/VIS spectrophotometer from Varian. The sensor molecule Gliadin is bound to the grating to sense the anti-Gliadin target agent. Before attachment of Gliadin to the carboxy (COOH) group of the HPDLC, the carboxy group is activated using the EDC/NHS coupling procedure. After activation of the groups, the Gliadin is attached. Following attachment, another protein, casein, is used to block carboxy groups that were not attached to Gliadin. Casein does not interfere with the target agent attachment, since the anti-Gliadin antibodies are specific for Gliadin.

In a second exemplary embodiment, a batch of HPDLC gratings are made on BK7 optical flats at 25-µm thickness. The gratings are evacuated over approximately three days to remove the liquid crystal. Certain gratings from the batch are checked with an ELISA (Enzyme Linked Immuno Specific Assay) kit, and other gratings are scanned in a spectrometer for a peak shift. The ELISA checked gratings and the spectrometer scanned gratings are tested with either standard A or standard F. The pre-selected spectral absorbance is proportional to concentration, i.e., A is the lowest concentration and F is the highest. The HPDLC gratings withstand treatment with all the solutions needed for protein and antibody attachment without degrading.

Exemplary embodiments involve a grating sensing anti-Gliadin, or an alternative embodiment sensing Cortisol. Materials used in the exemplary embodiments include the monomer dipentaerythritol hydroxy penta acrylate (DPHPA), photoinitiator dye Rose Bengal (RBAX), co-initiator N-phenylglycine (NVG), monomer N-vinylpyrrollidone (NVP), long-chain aliphatic acid dodecanoic acid (DDA), binding site monomer 2-carboxyethylacrylate (2-CEA), and liquid crystals E7 and TL213 (both available from Merck).

Gliadin, an antigen derived from wheat, is utilized as the sensor molecule to detect the presence of anti-Gliadin. The recipe includes 47.9% DPHPA, 0.6% RBAX, 1.5% NPG, 10.0% NVP, 38.0% E7, and 2.0% 2-CEA. The above formula, less the 2-CEA, is a conventional formulation for recording HPDLC gratings, and is given the designation CS573. A holographic recording in such a mixture results in a periodic distribution of interconnected liquid crystal droplets. The addition of 2-CEA provides COOH groups attached to the polymer matrix, with some COOH groups residing at the polymer/liquid crystal droplet interfaces. The pre-polymer mixture also includes 15 µm glass rods that act as spacers for the holographic cell which comprises two 1"-diameter, ⅛"-thick glass windows. A sonicator homogenizes the mixture prior to sandwiching the pre-polymer mixture within the holographic cell, between the glass windows. At least one of the glass windows is coated with a release agent to facilitate removal of one substrate after holographic recording. Alternatively, reflection holograms are recorded (in cells designated CS573-x, where x=1 . . . 9) using two 532-nm beams derived from the same frequency-doubled Nd:YVO$_4$ laser at an optical power of approximately 15 mW/cm$^2$ for 30 seconds. A 1-hour white-light post-cure procedure bleaches the remaining RBAX dye.

In a second exemplary embodiment, a batch of HPDLC gratings are made on BK7 optical flats at 25-μm thickness. The gratings are evacuated over approximately three days to remove the liquid crystal. Certain gratings from the batch are checked with an ELISA (Enzyme Linked Immuno Specific Assay) kit, and other gratings are scanned in a spectrometer for a peak shift. The ELISA checked gratings and the spectrometer scanned gratings are tested with either standard A or standard F. The pre-selected spectral absorbance is proportional to concentration, i.e., A is the lowest concentration and F is the highest. The HPDLC gratings withstand treatment with all the solutions needed for protein and antibody attachment without degrading.

Exemplary embodiments involve a grating sensing anti-Gliadin, or an alternative embodiment sensing Cortisol. Materials used in the exemplary embodiments include the monomer dipentaerythritol hydroxy penta acrylate (DPHPA), photoinitiator dye Rose Bengal (RBAX), co-initiator N-phenylglycine (NVG), monomer N-vinylpyrrollidone (NVP), long-chain aliphatic acid dodecanoic acid (DDA), binding site monomer 2-carboxyethylacrylate (2-CEA), and liquid crystals E7 and TL213 (both available from Merck).

Gliadin, an antigen derived from wheat, is utilized as the sensor molecule to detect the presence of anti-Gliadin. The recipe includes 47.9% DPHPA, 0.6% RBAX, 1.5% NPG, 10.0% NVP, 38.0% E7, and 2.0% 2-CEA. The above formula, less the 2-CEA, is a conventional formulation for recording HPDLC gratings, and is given the designation CS573. A holographic recording in such a mixture results in a periodic distribution of interconnected liquid crystal droplets. The addition of 2-CEA provides COOH groups attached to the polymer matrix, with some COOH groups residing at the polymer/liquid crystal droplet interfaces. The pre-polymer mixture also includes 15 μm glass rods that act as spacers for the holographic cell which comprises two 1"-diameter, ⅛"-thick glass windows. A sonicator homogenizes the mixture prior to sandwiching the pre-polymer mixture within the holographic cell, between the glass windows. At least one of the glass windows is coated with a release agent to facilitate removal of one substrate after holographic recording. Alternatively, reflection holograms are recorded (in cells designated CS573-x, where x=1 . . . 9) using two 532-nm beams derived from the same frequency-doubled Nd:YVO$_4$ laser at an optical power of approximately 15 mW/cm$^2$ for 30 seconds. A 1-hour white-light post-cure procedure bleaches the remaining RBAX dye.

Following post-cure, the release-agent-coated flat is separated from the photopolymerized material, and the transmittance spectrum of each photopolymerized material is measured using, for example, a Cary500 UV/VIS/NIR spectrometer. The nominal peak of the reflection notch (minimum of the transmittance curve) is around 535 nm. The holograms are placed in a vacuum oven (approximately 28 mm Hg) for a period of about 48 hours to extract the liquid crystal. After removing the holograms from the oven, the samples are rinsed in methanol and replaced in the oven for 3 hours. Each cell is then measured again in the Cary500. All samples exhibit a blue shift of the diffraction peak, indicating that the liquid crystal is removed, and the refractive index of the composite medium is decreased.

Following these measurements, six cells (x=2, 3, 5, 6, 8, 9) are selected for further tests and one additional cell (x=1) is reserved for a control experiment. The set of six cells are divided into two subsets of three (subset A: x=3, 5, 6 and subset B: x=2, 8, 9). Table 1 below describes the procedures applied to the cells. The binding of present antibodies, formation of the sandwich complexes, and enzymatic color reaction take place during three different reaction phases.

In Phase I, solution samples containing different concentrations of target molecules are pipetted onto the Bragg gratings. Any present target agents bind to the inner surface of the Bragg grating. After a 30-minute incubation the grating is washed with wash buffer for removing non-reactive components. Phase I includes incubation with Gliadin (I w/G) or no incubation with Gliadin (I w/o G).

TABLE 1

Processing of Bragg Gratings for Gliadin-Anti-Gliadin Tests[a]

| Subset | Grating | Phase I w/G | Phase I w/o G | IgA Incubation[b] | Phase II | Phase III |
|---|---|---|---|---|---|---|
| A | 3 | x | | 6 U/mL | | |
| A | 5 | x | | 6 U/mL | x | x |
| A | 6 | | X | 6 U/mL | x | x |
| B | 2 | x | | 31 U/mL | | |
| B | 8 | x | | 31 U/mL | x | x |
| B | 9 | | X | 31 U/mL | x | x |
| Control | 1 | | | NA | x | x |

[a]'x' denotes that part of the procedure that was used.
[b]Units/milliliter (U/mL) of IgA are the concentration units used by the supplier of the test kit.

After the Phase I treatment, sample Bragg gratings in subsets A and B are air-dried overnight. All sample Bragg gratings exhibit a red shift of the diffraction notch, with the non-Gliadin samples having about twice the shift of that of the Gliadin samples, due to the increased refraction index. In all cases, material, e.g., Gliadin and/or casein, is added to the vacant pores of the sample, attaching to the activated COOH sites, and thereby increasing the refractive index. The molecular weight of Gliadin is approximately 50,000 Daltons. Casein, a protein found in milk, exists most often as a micelle, with an average molecular weight of approximately 375,000 Daltons. Thus, sample Bragg gratings containing only casein have more mass and thus a higher refractive index than those sample Bragg gratings containing a mixture of casein and Gliadin. A higher refractive index implies a larger shift of the diffraction notch.

Figure 22:
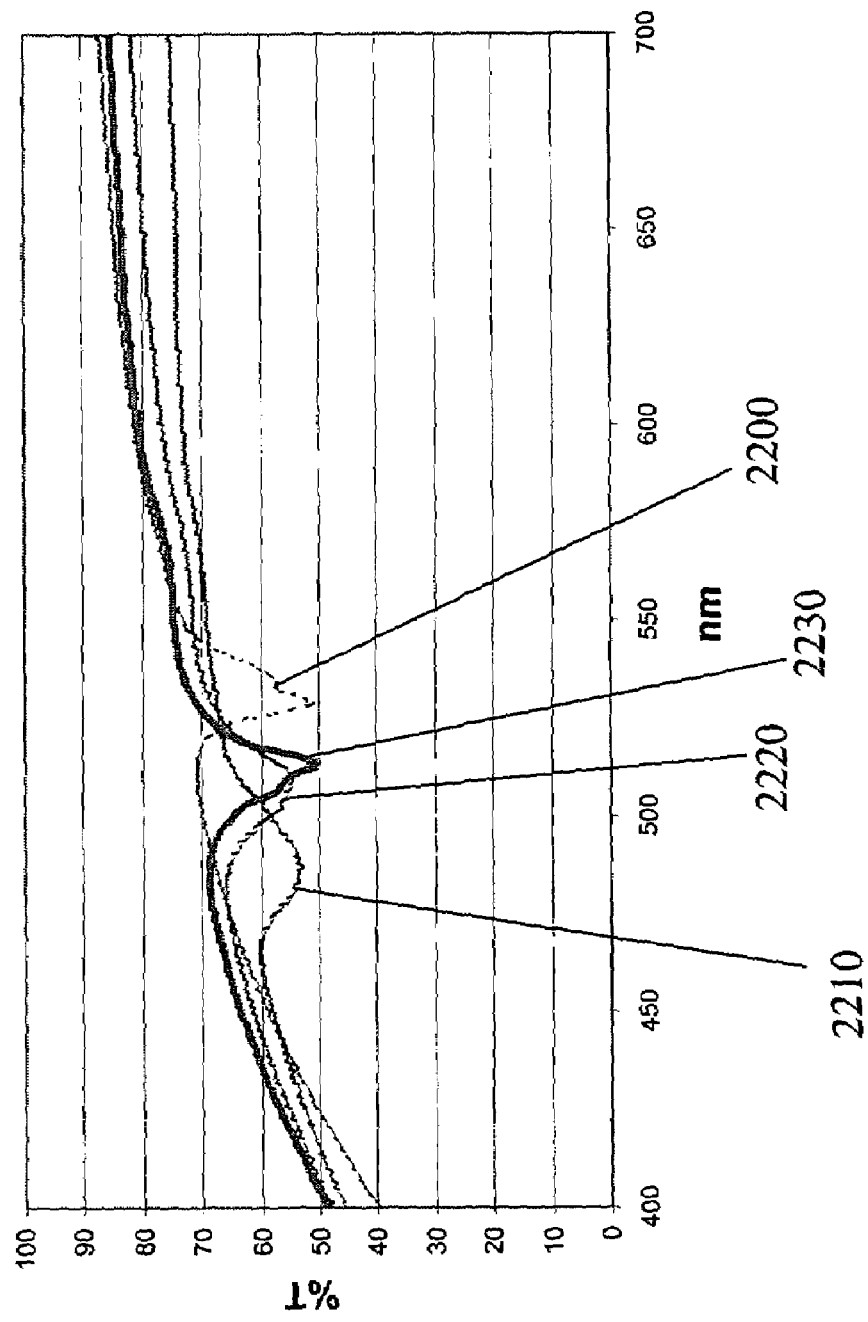
FIG. 22 shows transmission scans according to an embodiment of the present invention.

Following anti-Gliadin (IgA) incubation, sample Bragg gratings 3 and 2 are air-dried overnight. Both sample Bragg gratings exhibit an additional shift, indicating the binding of the anti-Gliadin to the Gliadin. All four spectrometer transmission scans in the above sequence for sample Bragg grating 3, as exemplified in FIG. 22, illustrate an initial scan 2200 after recording with liquid crystal droplets in the Bragg grating, a blue shifted scan 2210 after the pores are evacuated (liquid crystal removed), a subsequent red shift 2220 when Gliadin and casein are bound to the activated COOH sites, and a final red shift 2230 when the antibody binds to the Gliadin, thereby increasing the refractive index, i.e., adding mass to the pores. The final red shift 2230 is about 1%.

Sample Bragg grating 2 exhibits a final red shift of approximately 6%, a larger shift due to a higher concentration of antibodies.

Sample Bragg gratings 5, 6, 8, 9 and control 1 are subjected to Phases II and III of the procedure. In Phase II the sample Bragg gratings are incubated in an anti-human-IgA horseradish peroxidase conjugate solution, which recognizes IgA class antibodies bound to the immobilized antigens. A wash buffer then washes away any excess enzyme conjugate not specifically bound to the antibodies.

In Phase III, a chromogenic substrate solution containing TMB (3,3',5,5'-Tetramethylbenzidine) is dispensed onto the gratings. During incubation, the color of the solutions changes from a clear solution to blue. The addition of 1 M hydrochloric acid stops color development to stabilize the sample for spectrometer measurements. The solution changes color to yellow. The amount of color is proportional to the concentration of IgA antibodies present in the original sample. A higher concentration of IgA produces a larger absorbance at 450 nm. The color changes of sample Bragg gratings 5, 6, 8, 9 and control 1 are quantified by measuring the absorbance of the samples at 450 nm. In all cases, sample Bragg gratings 5 and 8, both treated with Gliadin, exhibit larger absorbance than cells not treated with Gliadin (6 and 9), with the larger difference being between sample Bragg gratings 8 and 9 that are exposed to the higher concentration of IgA. The control sample Bragg grating 1 exhibits an absorbance similar to sample Bragg grating 6, which follows since neither sample Bragg grating was treated with Gliadin. Finally, a solution of TMB and HCl is formed without any exposure to the sample Bragg gratings. This solution exhibits no absorbance at 450 nm.

In another exemplary embodiment, cortisol is the antigen and the sample Bragg grating is activated with anti-cortisol to form a detector sensitive to the presence of cortisol. Cortisol is a hormone present in the body and released in higher quantities during stressed or agitated states. Designated CS576, the recipe included 51.9% DPHPA, 0.6% RBAX, 1.5% NPG, 10.0% NVP, 4.0% DDA, 30.0% TL213, and 2.0% 2-CEA. The mixture also includes 8-µm glass rods as spacers for the holographic cell, and a sonicator homogenizes the mixture. The resulting syrup is then sandwiched between two 1"-diameter, ⅛"-thick glass windows. At least one of the glass windows is coated with a release agent to facilitate removing one of the substrates. Reflection holograms are prepared using 532-nm beams. A 1-hour white-light post-cure bleaches remaining RBAX dye. One substrate is removed from each of the sample Bragg gratings and the gratings are scanned in the Cary500. The nominal notch wavelength is 536 nm. After liquid crystal removal, the sample Bragg gratings are then split into four groups for further treatment: (A) anti-cortisol attachment with subsequent incubation in cortisol; (B) anti-cortisol attachment with no subsequent incubation in cortisol; (C) no antibody attachment with subsequent incubation in cortisol; and (D) anti-cortisol attachment with subsequent incubation in Gliadin. Two sample Bragg gratings from each group (A)-(D) are subjected to the entire cortisol test, consisting of attachment, incubation, spectrometer measurements of diffraction notch, and color test. The remaining two sample Bragg gratings from groups (A)-(D) are run only through the diffraction notch test.

Sample Bragg gratings in groups (A), (B), and (D) are subjected to the same attachment procedure, while no antibody (anti-cortisol) is added to the sample Bragg gratings in group (C). At the conclusion of these procedures, all of the sample Bragg gratings are measured using the Cary500. In all samples, the diffraction notch red shifts approximately 6% due to the increased refractive index as mass, i.e., anti-cortisol and/or casein, was added to the vacant pores.

Figure 23:
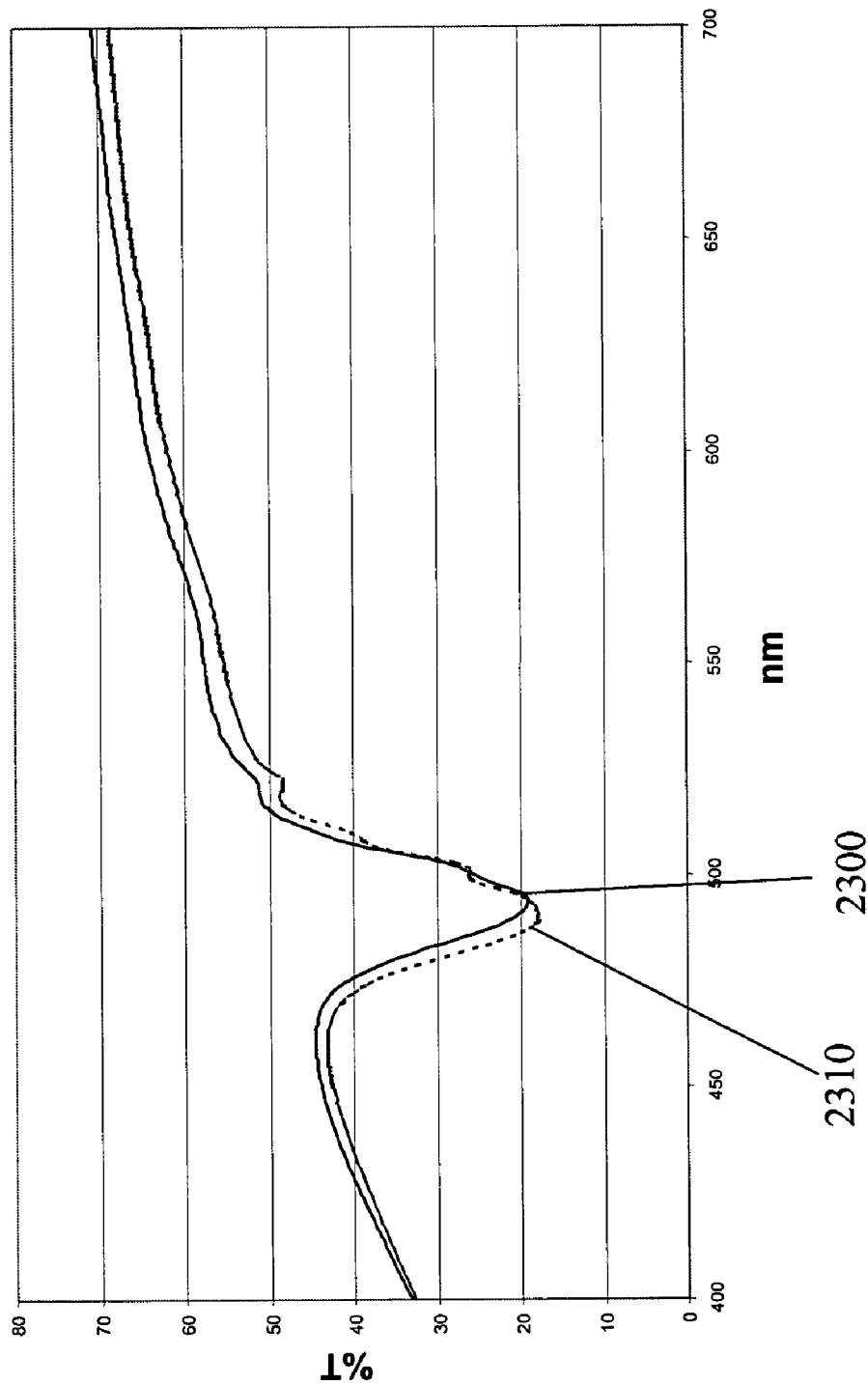
FIG. 23 shows a transmission scan according to an embodiment of the present invention.

Sample Bragg gratings in groups (A), (C), and (D) are then incubated in cortisol, and all sample Bragg gratings are re-measured with the Cary500. Only sample Bragg gratings in group (A) (the only group treated with anti-cortisol attachment and cortisol incubation) exhibit a red shift (approximately 1%), indicating the binding of cortisol to anti-cortisol thereby increases the mass in the pores and thus increasing the refractive index. FIG. 23 exemplifies this shift when an anti-cortisol activated grating 2300 is incubated in cortisol 2310.

Figure 24:
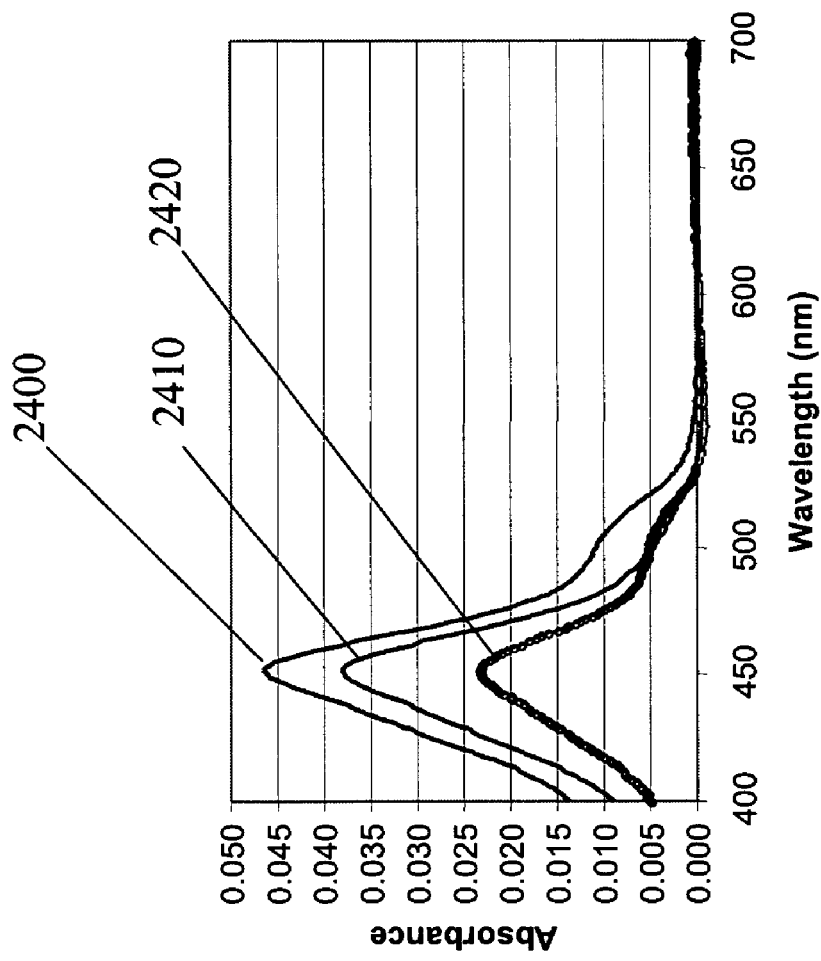
FIG. 24 shows a relation of absorbance to a concentration of antigen according to an embodiment of the present invention.

Two sample Bragg gratings from groups (A), (B), and (C) are subjected to a color test verification. The color test consists of a competitive reaction between the antigen, i.e., cortisol, and an enzyme-conjugated antigen, i.e., anti-cortisol. Sample Bragg gratings in groups (A) and (C) are incubated in equal volumes of the antigen and the enzyme-conjugated antigen, while group (B) sample Bragg gratings are incubated in the enzyme-conjugated antigen only. Antigen and enzyme-conjugated antigen molecules bind with present antibodies in proportion to their relative concentration. When the chromogenic solution containing TMB is added, TMB reacts with the enzyme-conjugated antigen, inducing a color change. HCl is again added to stop the reaction and stabilize the sample Bragg gratings for subsequent spectrometer runs. Hence, sample Bragg gratings with a higher proportion of enzyme-conjugated antigens exhibit a stronger color change, i.e., have a higher absorbance at 450 nm. Thus, the absorbance at 450 nm is inversely proportional to the concentration of antigen, i.e., cortisol, present, as exemplified in the test results in FIG. 24. The highest absorbance is for a sample 2400 not incubated in cortisol because only enzyme-conjugated antigen binds to the present antibodies. Sample Bragg grating 2410 incubated in cortisol exhibits a lower absorbance, i.e., some of the antibody sites are bound with cortisol and some with enzyme-conjugated antigen. Sample Bragg grating 2420 that was not treated with antibody attachment shows the least absorbance, i.e., there are no sites for the enzyme-conjugated antigen to bind to and hence produces a color change.

The embodiments described herein are intended to be exemplary, and while including and describing the best mode of practicing, are not intended to limit the invention. Those skilled in the art appreciate the multiple variations to the embodiments described herein which fall within the scope of the invention.

What is claimed is:

1. A method of determining the presence of a target agent in an environment, comprising the steps of:
    obtaining a first sample from the environment;
    introducing the first sample to at least one detection module;
    filtering the first sample through at least a first filter and a second filter which are part of the at least one detection module, wherein the first filter and the second filter comprise porous Bragg gratings, further wherein the first filter contains at least one detection molecule for binding the target agent thereto and the second filter contains no detection molecules for binding the target agent thereto;
    measuring an optical property of the first filter and the second filter after filtering the first sample therethrough;
    comparing the measured optical property of the first filter to the measured optical property of the second filter to determine a presence of the target agent;

measuring an optical property of a third filter which is not exposed to the first sample, the third filter comprising a porous Bragg grating; and comparing the measured optical property of the third filter to the measured optical property of the first and second filters to determine a presence of spurious signals caused by the environment.

2. The method of claim 1, wherein the Bragg gratings are formed by holographically polymerizing a polymer-dispersed liquid crystal material.

3. The method of claim 2, wherein the Bragg grating is fabricated holographically for apodization.

4. The method of claim 1, further comprising the step of adding a sample to a working fluid, wherein the working fluid, including the sample, is introduced to the at least one detection module.

5. The method of claim 4, further comprising the step of recirculating the working fluid to obtain a second sample from the environment.

6. The method of claim 1, wherein measuring the optical property of the first filter and the second filter includes determining a change in refractive index of the first filter and second filter.

7. The method of claim 1, further comprising the step of storing data of the measured properties of the first filter and the measured properties of the second filter indicative of the presence of the target agent.

8. A sensor for determining the presence of at least one target agent in a sample comprising:
a collector system for collecting the sample from an environment;
a transfer system for adding the sample to a working fluid;
a dispenser system for introducing the working fluid, including the sample, to a detector system; and
a detector system comprising at least one detector module that includes:
at least a first optical grating, a second optical grating, and a third optical grating, wherein the first optical grating, the second optical grating, and third optical grating are porous Bragg gratings, further wherein the first optical grating contains at least one detector molecule for binding the at least one target agent thereto and the second optical grating does not contain a detector molecule for binding the at least one target agent thereto, the third optical grating being isolated and not in contact with the working fluid;
at least a first measuring device for measuring an optical response of the first optical grating after contact with the working fluid, including the sample,
at least a second measuring device for measuring an optical response of the second optical grating after contact with the working fluid, including the sample,
at least a third measuring device for measuring an optical response of the third optical grating, and
a processor for comparing the measured optical response from the at least a first measuring device to the measured optical response from the at least a second measuring device to determine a presence of the at least one target agent, for comparing the measured optical response from the third filter to the measured optical response from the first and second filters to determine a presence of spurious signals caused by surroundings of the sensor.

9. The sensor according to claim 8 further comprising a data storage system for storing data indicative of the presence of the at least one target agent.

10. The sensor according to claim 9 further comprising a transmission system for transmitting the data indicative of the presence of the at least one target agent to an analysis location.

11. The sensor according to claim 8 further comprising a recirculation system for receiving the working fluid, including the sample, from the at least one detector module and removing the sample therefrom in order to re-use the working fluid with another sample from the collector system.

12. The sensor of claim 8, wherein the Bragg gratings are formed of a holographically polymerized polymer-dispersed liquid crystal material.

13. The sensor of claim 12, wherein the polymer-dispersed liquid crystal material comprises, prior to holographic polymerization:
(a) a polymerizable monomer;
(b) a liquid crystal;
(c) a cross linking monomer;
(d) a coinitiator;
(e) a photoinitiator dye; and
(f) a binding site monomer.

14. The sensor of claim 8, wherein the at least a first measuring device and the at least a second measuring device are photodetectors.

15. The sensor of claim 8, wherein the at least one detector module further comprises:
a first inlet reservoir integrally connected to a first micro-fluidic channel for providing the working fluid, including the sample, to the at least a first optical grating; and
a second inlet reservoir integrally connected to a second micro-fluidic channel for providing the working fluid, including the sample, to the at least a second optical grating.

16. The sensor of claim 15 further comprising a light source optically coupled to a waveguide for providing light to the at least a first optical grating and the at least a second optical grating.

17. A detector module for detecting a target agent within a sample, the detector module comprising:
a first and second inlet reservoir for receiving a working fluid containing the sample therein;
a first micro-fluidic channel integrally connected to the first inlet reservoir;
a second micro-fluidic channel integrally connected to the second inlet reservoir;
a first optical grating physically integrated with the first micro-fluidic channel and a second optical grating physically integrated with the second micro-fluidic channel, wherein the first optical grating and the second optical grating comprise porous Bragg gratings, further wherein the first optical grating includes at least one detector molecule for binding the target agent within the sample thereto and the second optical grating does not include a detector molecule for binding the target agent within the sample thereto;
a third optical grating which is isolated from the working fluid, the third optical grating comprising a porous Bragg grating; and
at least one outlet reservoir physically integrated with the first and second micro-fluidic channels for removing the working fluid containing the sample from the detector module in order to re-use the working fluid with another sample.

18. The detector module of claim 17 further comprising:
a substrate formed of a first material; and
a second material formed on at least part of the substrate, wherein the at least one inlet reservoir, the first micro-fluidic channel, the second micro-fluidic channel, the first optical grating, the second optical grating and the at least one outlet reservoir are formed in the second material.

19. The detector module of claim 18, wherein the first material is silicon.

20. The detector module of claim 18, wherein the second material is silicon dioxide.

21. The detector module of claim 18 further comprising a waveguide formed of a third material and optically integrated with the first and second optical gratings.

22. The detector module of claim 21, wherein the third material is silicon oxynitride.

23. The detector module of claim 21, wherein the waveguide is split into a first arm that is optically integrated with the at least a first optical grating and a second arm that is optically integrated with the second optical grating.

24. The detector module of claim 21 further comprising;
a light source optically coupled to the waveguide;
a first photodetector located in an optical path of the waveguide and an optical path of the first optical grating; and
a second photodetector located in the optical path of the waveguide and an optical path of the second optical grating.

25. The detector module of claim 23 further wherein the third optical grating is located in a third arm of the waveguide, wherein the third optical grating does not contact the sample.

26. The detector module of claim 17, wherein the first and second optical gratings are formed of a holographically polymerized polymer-dispersed liquid crystal material comprising, prior to holographic polymerization:
(a) a polymerizable monomer;
(b) a liquid crystal;
(c) a cross linking monomer;
(d) a coinitiator;
(e) a photoinitiator dye; and
(f) a binding site monomer.

27. The detector module of claim 17 further comprising:
a substrate formed of a first material;
a second material formed on at least part of the substrate having a waveguide formed therein of a third material; and
a fourth material formed on at least part of the second material wherein the at least one inlet reservoir, the first micro-fluidic channel, the second micro-fluidic channel, the first optical grating, the second optical grating and the at least one outlet reservoir are formed in the fourth material.

28. The detector module of claim 27, wherein the first material is silicon.

29. The detector module of claim 27, wherein the second material is $SiO_2$.

30. The detector module of claim 27, wherein the third material is silicon oxynitride.

31. The detector module of claim 27, wherein the fourth material is a polymer.

32. The method of claim 1, wherein the spurious signals comprise fluctuations due to one of: thermal drift of at least one of the filters and light source changes.

33. The sensor according to claim 8, wherein the spurious signals comprise fluctuations due to one of: thermal drift of at least one of the filters and light source changes.

34. The detector module of claim 17, wherein the third optical grating is used to determine a presence of spurious signals caused by the environment.

35. The detector module of claim 34, wherein the spurious signals comprise fluctuations due to one of: thermal drift of at least one of the filters and light source changes.

* * * * *